United States Patent
Iravanian

(10) Patent No.: US 10,629,308 B1
(45) Date of Patent: Apr. 21, 2020

(54) CARDIAC ELECTROPHYSIOLOGY SIMULATOR

(71) Applicant: Shahriar Iravanian, Atlanta, GA (US)

(72) Inventor: Shahriar Iravanian, Atlanta, GA (US)

(*) Notice: Subject to any disclaimer, the term of this patent is extended or adjusted under 35 U.S.C. 154(b) by 982 days.

(21) Appl. No.: 14/930,446

(22) Filed: Nov. 2, 2015

Related U.S. Application Data

(60) Provisional application No. 62/074,216, filed on Nov. 3, 2014, provisional application No. 62/181,618, filed on Jun. 18, 2015.

(51) Int. Cl.
 *G09B 9/00* (2006.01)
 *G16H 50/50* (2018.01)
 *G06F 17/10* (2006.01)

(52) U.S. Cl.
 CPC .......... *G16H 50/50* (2018.01); *G06F 17/10* (2013.01); *G09B 9/00* (2013.01)

(58) Field of Classification Search
 CPC .......... G16H 50/50; G06F 17/10; G09B 9/00; G09B 19/00; G09B 23/00
 See application file for complete search history.

(56) References Cited

U.S. PATENT DOCUMENTS

| 4,639,223 A * | 1/1987 | Keller, Jr. ............... | G09B 23/28 434/272 |
|---|---|---|---|
| 5,137,458 A * | 8/1992 | Ungs ..................... | G09B 23/288 434/262 |

(Continued)

FOREIGN PATENT DOCUMENTS

EP 1 543 865 B1 9/2008

OTHER PUBLICATIONS

Dit Hennig "Time series analysis and modeling of the statistical properties of heart beat dynamics during atrial fibrillation" Technische Universitat Ilmenau, Doctoral Dissertation on Jan. 21, 2009 nbn:de:gbv:ilm1 -2009000443 < https://www.db-thueringen.de/servlets/MCRFileNodeServlet/dbt_derivate_00020352/ilm1 -2009000443.pdf>.*

(Continued)

*Primary Examiner* — Robert J Utama
(74) *Attorney, Agent, or Firm* — Knobbe, Martens, Olson & Bear LLP

(57) ABSTRACT

Systems, devices, and methods to simulate cardiac electrophysiological scenarios are disclosed. Embodiments use processor-controlled state machines that provide dynamically programmable timing periods of nodes representing structural portions of the heart and links representing conduction pathways. The timing periods include refractory periods, conduction delays, and cycle lengths for areas of cardiac tissue that automatically or spontaneously generate electrical impulses. The timing periods can be dynamically calculated and reset based on a function of a node's current cycle length and/or diastolic interval, among other things. A special-purpose hardware interface board interfaces with an EP recording system and is configured to detect, convert, and condition simulated cardiac signals transmitted to and received from the EP recording system. Pacing spikes can be detected by the system. Simulated surface ECG and IEGM signals are displayed to the user on a workstation. The user may issue instructions to modify the electrophysiological scenarios.

13 Claims, 22 Drawing Sheets

(56) References Cited

U.S. PATENT DOCUMENTS

| | | | |
|---|---|---|---|
| 5,503,149 A | 4/1996 | Beavin | |
| 5,509,927 A | 4/1996 | Epstein et al. | |
| 5,692,907 A * | 12/1997 | Glassel | G16H 50/50 434/262 |
| 5,782,885 A * | 7/1998 | Andersson | A61N 1/365 607/17 |
| 6,193,519 B1 | 2/2001 | Eggert et al. | |
| 6,918,771 B2 | 7/2005 | Arington et al. | |
| 7,039,893 B2 * | 5/2006 | DenBraber | G06F 17/5045 716/117 |
| 7,050,857 B2 | 5/2006 | Samuelsson et al. | |
| 7,274,959 B1 | 9/2007 | Wang et al. | |
| 7,822,475 B2 | 10/2010 | Schomburg et al. | |
| 7,963,924 B2 * | 6/2011 | Rom | G16H 50/50 600/508 |
| 8,608,484 B2 | 12/2013 | Kalafut et al. | |
| 8,650,415 B2 * | 2/2014 | Ruiter | A61B 5/021 600/485 |
| 8,682,427 B2 | 3/2014 | Doerr | |
| 8,834,172 B2 | 9/2014 | Rubinstein et al. | |
| 9,507,912 B2 * | 11/2016 | Kaula | G06F 19/34 |
| 2008/0103744 A1 * | 5/2008 | Rom | G16H 50/50 703/11 |
| 2008/0154142 A1 * | 6/2008 | Lundback | G16H 50/50 600/508 |
| 2009/0005845 A1 * | 1/2009 | David | A61N 1/0558 607/122 |
| 2009/0226867 A1 * | 9/2009 | Kalafut | G09B 23/32 434/268 |
| 2009/0263324 A1 * | 10/2009 | Sugiyama | A01K 67/027 424/9.2 |
| 2010/0281413 A1 * | 11/2010 | Lundback | G09B 23/288 715/771 |
| 2011/0046935 A1 * | 2/2011 | Sugaya | G06F 19/3481 703/11 |
| 2013/0226542 A1 * | 8/2013 | Rapaka | G06F 17/5009 703/2 |
| 2013/0330701 A1 * | 12/2013 | Rubinstein | G09B 23/285 434/272 |
| 2014/0004494 A1 * | 1/2014 | Griesser | A61N 1/3993 434/267 |
| 2014/0022250 A1 * | 1/2014 | Mansi | G06T 19/20 345/420 |
| 2014/0093853 A1 | 4/2014 | Constantine | |
| 2016/0058520 A1 * | 3/2016 | Yang | G16H 50/50 703/11 |

OTHER PUBLICATIONS

Ahlfeldt, H. et al., *Computer Simulation of Cardiac Arrhythmias*, Department of Medical Informatics, Linköping University, Sweden and Institute of Medical Electronics, University of Tokyo, Japan, Computers and Biomedical Research 20, 305-323 (1987), 19 pp.

Ahlfeldt, H. et al., *Computer Simulation of Cardiac Pacing*, Pacing and Clinical Electrophysiology, Feb. 1988; vol. 11, No. 2, 174-184, 13 pp.

Iravanian, Shahriar, *EPS 101, Supraventricular Tachycardia Simulator (SVTSIM)*, dated Jul. 23, 2013, http://wvtsim.com/eps.html (downloaded Nov. 1, 2015), 41 pp.

Iravanian, Shahriar, *Supraventricular Tachycardia Simulator (svtsim): Documentation*, dated Aug. 16, 2011, http://svtsim.com/svisim_doc.html (dowloaded Oct. 30, 2015), 4 pp.

Iravanian, Shahriar, *Supraventricular Tachycardia Simulator (SVTSIM): Diagnostic Maneuvers*, dated Jul. 6, 2013, http://svtsim.com/doc/svt.html (downloaded Oct. 30, 2015), 10 pp.

Iravanian, Shahriar, *Supraventricular Tachycardia Simulator (SVTSIM) Quiz*, dated Aug. 29, 2015, http://svtsim.com/quiz.html (downloaded Oct. 20, 2015), 8 pp.

Iravanian, Shahriar, *Supraventricular Tachycardia Simulator (SVTSIM)*, dated Jun. 13, 2013, http://svtsim.com/doc/whatsnew.html (downloaded Oct. 30, 2015), 2 pp.

Iravanian, Shahriar, *Supraventricular Tachycardia Simulator (SVTSIM)*, dated 2011, http://svtsim.com/svtsim.html (downloaded Oct. 30, 2015), 1 pp.

Iravanian, Shahriar, *Supraventricular Tachycardia Simulator (SVTSIM) User's Manual*, dated Jul. 6, 2013, http://svtsim.com/doc/svtsim_manual.html (downloaded Nov. 1, 2015), 5 pp.

Iravanian, Shahriar, *Cardiac Hemodynamic Simulator (HEMOSIM)*, dated Aug. 15, 2013, http://svtsim.com/hemosim.html (downloaded Oct. 30, 2015), 1 pp.

Steinhaus, Bruce M. et al., *A PC-Based Real-time Simulator of Cardiac Bradycardia and Tachycardia Arrhythmias*, Telectronics Pacing Systems, Englewood, Colorado, USA (1992) IEEE, 587-590, 4 pp.

\* cited by examiner

CARDIAC ELECTROPHYSIOLOGY SIMULATOR

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application claims priority benefit under 35 U.S.C. § 119(e) from, and is a nonprovisional application of U.S. Provisional Patent Application Ser. No. 62/074,216 filed on Nov. 3, 2014, entitled Cardiac Electrophysiology Simulator, and U.S. Provisional Patent Application Ser. No. 62/181,618, filed on Jun. 18, 2015, entitled Cardiac Electrophysiology Simulator, both of which are incorporated herein by reference in their entireties.

BACKGROUND

The present application discloses systems, apparatuses, and methods directed to an interactive, intracardiac signal simulator that emulates the electrical behavior of a patient's heart. In particular, the disclosed interactive, intracardiac signal simulator may be used in the course of a simulated electrophysiology study (EP study).

An EP study is an invasive procedure used to evaluate a patient's heart rhythms. Motivations for conducting EP studies include evaluating patient symptoms such as lightheadedness, fainting, weakness, dizziness, palpitations, or other cardiac rate or rhythmic issues, locating a source of a patient's cardiac rhythm problem, assessing the therapeutic effectiveness of one or more medications to treat an arrhythmia, and/or to deliver therapeutic treatment for a cardiac rhythmic disorder. During the EP study, wire electrodes are inserted through a vein in, e.g., the patient's groin or neck. The electrodes track the vein to reach the interior of the patient's heart, where the electrodes are used to measure the patient's cardiac electrical activity. Electrical stimulation signals may also be transmitted to the patient's heart to initiate suspected or previously-observed abnormal heart rhythm disorders for evaluation. Sometimes an abnormal rhythm is intentionally stimulated by the electrophysiologist to identify the underlying, structural problem with the patient's heart or to evaluate the effectiveness of a pharmaceutical therapy. The electrophysiologist may also map the electrical activity of the patient's cardiac tissue to locate a source of the patient's arrhythmia. If a source location of the arrhythmia is identified, a corrective procedure, such as an ablation, may be performed in an effort to resolve the problem. Since the findings of the EP study provide insight into the electrical behavior of the patient's heart, those findings may assist the electrophysiologist in identifying additional therapeutic measures to address the patient's conditions.

Clinically, a cardiac electrophysiologist (the operator) performs the EP study by placing multi-electrode catheters in the heart for recording intracardiac electrical signals, also referred to as intracardiac electrograms (IEGMs). The catheters are connected to an electrophysiology recording system (also referred to herein as "an EP recording system"). Commercial electrophysiology recording systems include, among others, Cardiolab™ offered by GE Healthcare, and EP-WorkMate™ Claris™, offered by St. Jude Medical, Inc. Examples of electrophysiology recording systems are disclosed in U.S. Patent Publication No. US 2015/0058032, entitled "System for Sharing Data Within an Electrophysiology Lab," published on Feb. 26, 2015, and U.S. Patent Publication No. US 2013/0041243, entitled "User Interface Devices for Electrophysiology Lab Diagnostic and Therapeutic Equipment," published on Feb. 14, 2013, the contents of which are incorporated herein by reference in their entireties. In addition to recording and reviewing signals, the operator interacts with the patient's heart by pacing (delivery of low voltage pulses through catheters to specific cardiac regions), infusion of medications, and/or cardioversion (delivery of one or more electrical shocks to terminate dangerous arrhythmias). The goal of the EP study is to test the patient's cardiac electrical system and to diagnose its abnormalities (arrhythmias). In many cases, the EP study is a prelude to a corrective procedure, such as ablation.

The ability to perform and interpret an EP study is a necessary skill for electrophysiologists. While there is no perfect substitute for performing tests and maneuvers during an EP study conducted on a human patient, logistical and safety considerations commonly preclude a thorough practice in the course of a routine case. As a result, the operator may gradually lose his or her skills needed to deal with difficult cases.

Electrophysiology lab staff members, such as nurses and technicians, play integral roles in an EP study. The staff members are required to possess a very good working knowledge of the intracardiac signals and pacing maneuvers used in EP studies. Traditionally, staff members learn EP study skills on-the-job, over the course of many years, which can be both inefficient and potentially hazardous for patients.

Acquiring and maintaining complex skill sets can be facilitated by using simulators, which allow the operator to practice in a safe and controlled setting. For example, flight simulators are commonly used in the aviation industry for pilot training and are considered a valuable part of pilot training programs. More recently, simulators have entered the medical field and are gradually becoming an integrated part of clinical skill training and competency assessment.

Currently-available electrocardiography (ECG) simulators simply play back a previously-recorded set of signals. Such passive systems are not sufficient for simulating intracardiac signals because they lack the ability to interact with the cardiac electrical system in real-time, which can be an important component of an EP study and an EP study training session.

SUMMARY

One aspect of the disclosed interactive simulation system, in some embodiments, is the presence of a dynamic cardiac model that encapsulates how the operator envisions the cardiac electrical system. In some embodiments, the disclosed interactive, intracardiac signal simulator connects to an electrophysiology recording system, emulates intracardiac signals (as normal rhythms or as abnormal arrhythmias), detects an operator's inputs, e.g., in the form of pacing stimuli, cardioversion, and/or administration of medication, and updates the dynamic cardiac model accordingly.

Another aspect of the disclosed interactive, intracardiac signal simulator, in some embodiments, is the ability of the trainee to function in an environment that closely and realistically reflects an actual EP study. The operator uses an EP recording system and various external pacemakers during an EP study. A simulator that feeds signals directly to the clinical EP recording system and receives signals from the clinical EP recording system (including stimulation signals from, for example, a clinical pacemaker) is closer to the manner by which an EP study is performed. Such an in-system simulation, where the simulated intracardiac electrocardiogram is integrated into actual clinical equipment, helps the clinician being trained to develop a sense and feel for the operation, management, and control of the equipment in the electrophysiology lab, (such as, by way of non-limiting example, the EP recording system, pacemakers, and defibrillators).

In an aspect of the present disclosure, a cardiac simulation system may include a simulation processor configured to simulate electrical behavior of a patient's heart, an EP system interface, in communication with the simulation processor, the EP system interface configured transmit signals to and receive signals from an electrophysiological recording system, a user interface in communication with the simulation processor, and a cardiac model. The cardiac model is configured to execute on the simulation processor and includes a plurality of state machines that are controlled by the simulation processor. Each state machine comprises a node configured to be switchable between a node resting state and a node refractory state. Each node is configured to transmit a state transition signal. The node includes a node refractory period and a node cycle period. In response to the node switching from the node resting state to the node refractory state, the node refractory period is dynamically determined by calculating a node refractory waiting time based on a node refractory function, and the node cycle length is dynamically determined by calculating a node cycle waiting time based on a node cycle function. The node refractory function may be based on, at least in part, a current node cycle length, a current node diastolic interval, or a random process. Similarly, the node cycle time function may be based on, at least in part, a current node cycle length, a current node diastolic interval, or a random process.

The cardiac simulation system may also include a link configured to be switchable between a link resting state, a link waiting state, and a link refractory state. The link includes a link refractory period and a link conduction delay. In response to the link switching from the link resting state to the link waiting state, the link refractory period is dynamically determined by calculating a link refractory waiting time based on a link refractory function, and the link conduction delay period is dynamically determined by calculating a link conduction delay waiting time based on a link conduction delay function. The link refractory function may be based on, at least in part, a current node cycle length, a current node diastolic interval, or a random process. Similarly, the link conduction delay function may be based on, at least in part, a current node cycle length, a current node diastolic interval, or a random process.

According to an embodiment, a simulation system for simulating the electrical behavior of a patient's heart is disclosed. The system includes a single board computer having a processor, a memory device, a storage device, an input/output device, and a network interface device. The system also includes a hardware interface board, in communication with the single board computer and with an electrophysiological recording system. The hardware interface board is configured to detect, convert, and condition simulated cardiac signals transmitted to and received from the electrophysiological recording system. Also included in the system is a user interface, having a display device, in communication with the simulation processor. The system also includes a cardiac model, configured to execute on the single board computer, comprising a state machine configured to represent a structural portion of a patient's heart. The state machine is switchable between a resting state and a refractory state, and includes a timer having a programmable time period. In response to the state machine switching from the resting state to the refractory state, the programmable time period is dynamically determined and reset, and in response to expiration of the time period, the timer transmits a state transition signal.

In some embodiments, the programmable time period is dynamically determined based, at least in part, on a current cycle length of the state machine, a current diastolic interval of the state machine, or on a random process. In some embodiments, the programmable time period is dynamically determined based on, at least in part, an exponential decay function having a decay rate that depends, at least in part, on the current cycle length of the state machine, the current diastolic interval of the state machine, or both the current cycle length and the current diastolic interval of the state machine. In some embodiments, the programmable time period is dynamically determined based, at least in part, on a random process, such as, by way of non-limiting example, a uniform distribution.

In accordance with certain embodiments, the simulation system is configured to generate one or more simulated cardiac signals and transmit the one or more signals to the user interface and to the hardware interface board. In some embodiments, the simulation system includes a stimulation detection module, configured to execute on the single board computer, which compares a signal received from the electrophysiological recording system with the generated simulated cardiac signal. In response to a determination that the compared signals differ beyond a predetermined threshold, a notification that a pacing pulse has been detected is transmitted to the cardiac model. The simulation model may also include a visualization module, configured to execute on the single board computer, which generates a simulated surface electrocardiogram signal and a simulated intracardiac electrocardiogram signal and transmits the simulated signals to the user interface to be presented on the display device.

According to another embodiment, a method for simulating the electrical behavior of a heart is disclosed. The method includes defining a plurality of structural portions of a cardiac anatomy to be simulated. A state machine is associated with each of the defined structural portions of the cardiac anatomy. The associated state machines are configured to execute on a single board computer comprising a processor, a memory device, a storage device, an input/output device, and a network interface device. Each associated state machine is switchable between a resting state and a refractory state. A refractory timer is associated with each state machine. The refractory timer has a programmable refractory timing period and is configured to time the expiration of the refractory timing period in response to a transition of the associated state machine to the refractory state. In response to the transition of the associated state machine to the refractory state, the refractory timing period is reset based on, at least in part, a current cycle time of the associated state machine, a current diastolic interval of the associated state machine, both the current cycle time and the current diastolic interval of the associated state machine, or a random process. In certain embodiments, resetting the refractory timing period is based on, at least in part, an exponential decay function having a decay rate that depends, at least in part, on a current cycle time of the associated state machine, a current diastolic interval of the associated state machine, both the current cycle time and the current diastolic interval of the associated state machine, or a random process.

According to some embodiments, the method includes associating, for each associated state machine, a cycle length timer having a dynamically programmable cycle length timing period. The cycle length timer may be configured to time the expiration of the cycle length timing period in response to a transition of the associated state machine to the resting state. In response to a transition of the associated state machine to the resting state, the cycle length timing period is reset. Determination of the reset cycle length timing period is based on, at least in part, a current cycle time of the associated state machine, a current diastolic interval of the associated state machine, both the current cycle time and the current diastolic interval of the associated state machine, or a random process. Determination of the reset cycle length timing period may also be based on, at least in part, an exponential decay function having a decay rate that depends on, at least in part, a current cycle time of the associated state machine, a current diastolic interval of the associated state machine, both the current cycle time and the current diastolic interval of the associated state machine, or a random process.

Another aspect of the method includes detecting the states of the associated state machines, and generating a simulated surface electrocardiogram (ECG) and a simulated intracardiac electrogram (IEGM) based on the detected states of the associated state machines. The method also includes transmitting, to an instructor workstation and to a hardware interface board, the simulated surface and intracardiac electrogram signals, and displaying, on the instructor workstation, the simulated surface and intracardiac electrogram signals. The method also includes processing, on the hardware interface board, the simulated surface ECG and IEGM signals, and transmitting the processed simulated surface ECG and IEGM signals from the hardware interface board to an electrophysiological recording system.

In some embodiments, the method includes receiving, from the electrophysiological recording system, a plurality of EP signals reflective of signals received by the electrophysiological recording system. The method includes comparing the received EP signals with the transmitted processed simulated surface ECG and IEGM signals and determining, in response an assessment that the compared signals differ beyond a predetermined threshold, that a pacing stimulus has been detected.

The method may also include receiving, from the instructor workstation, an instruction to modify at least one of the plurality of associated state machines and modifying, in response to the instruction, the at least one of the plurality of associated state machines.

For purposes of summarizing the disclosure, certain aspects, advantages, and novel features have been described herein. Of course, it is to be understood that not necessarily all such aspects, advantages, or features will be embodied in any particular embodiment of the present disclosure.

DETAILED DESCRIPTION

Figure 1A:
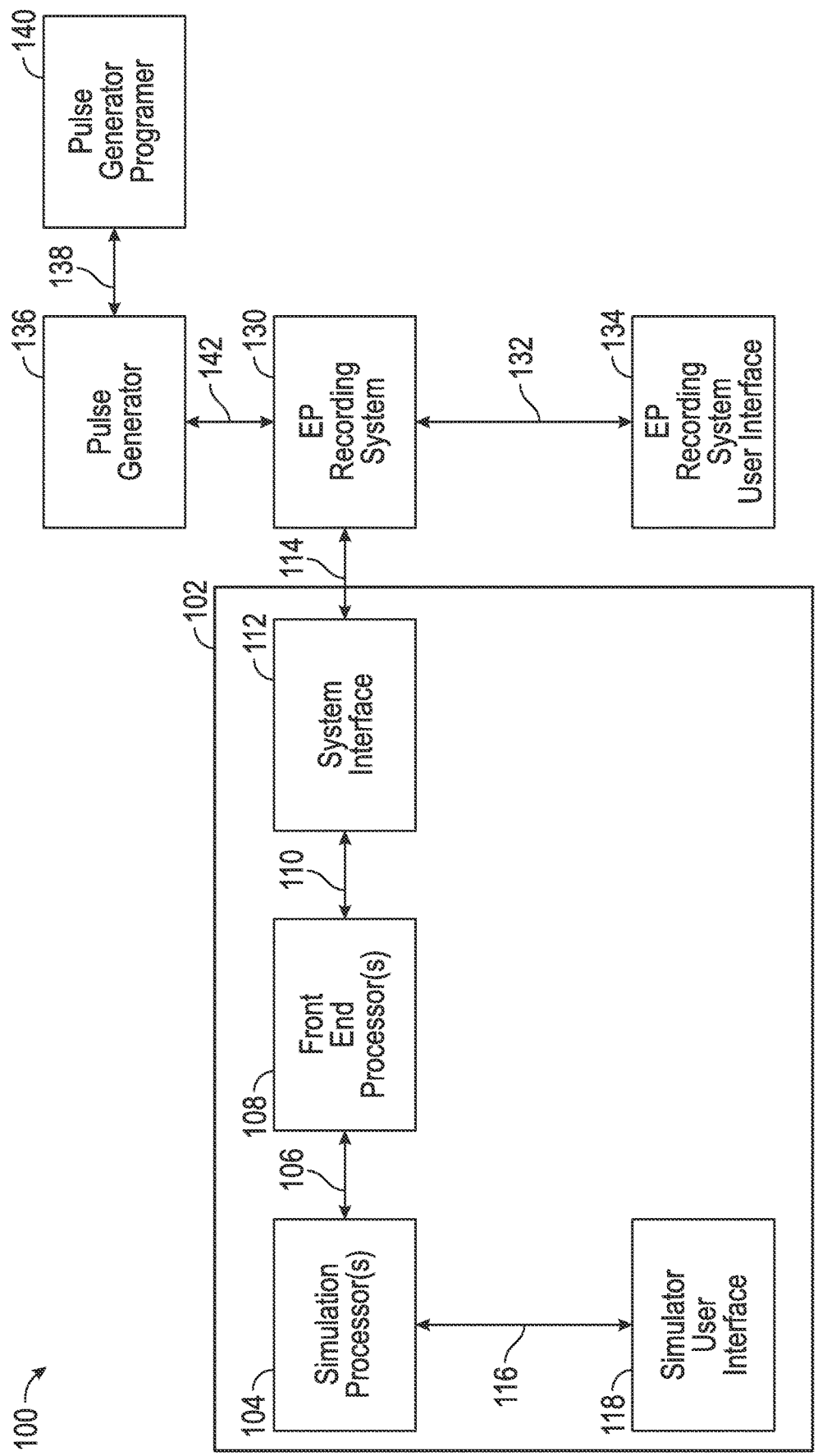
FIG. 1A is a simplified hardware block diagram of an intracardiac simulation system according an embodiment of the present disclosure.

The following description is merely illustrative in nature and is in no way intended to limit the disclosure, its application, or uses. For purposes of clarity, the same reference numbers may be used in the drawings to identify similar elements. It should be understood that steps within a method may be executed in different order without altering the principles of the present disclosure.

The present disclosure describes systems, devices, methods, and non-transitory computer readable media to simulate, among other things, electrophysiological tachycardia scenarios. Embodiments of the present disclosure use software-implemented and software-controlled state machines that provide timing periods of nodes and links (e.g. refractory periods, conduction delays, and cycle lengths for automatic foci and other areas of cardiac tissue that spontaneously generate electrical impulses) that can be dynamically set as a function of the previous cycle length and/or the previous diastolic interval. This flexibility allows the system to easily emulate phenomena such as, for example, decremental conduction, rate-adaption of refractoriness, and paced suppression of automatic foci, among other phenomena, which are necessary for simulation of complex arrhythmias, such as, for example, tachycardias. Advantageously, the disclosed intracardiac simulation system reflects the manner by which a clinical electrophysiologist conceptualizes the cardiac electrical system. Clinical concepts, such as refractory period, conduction delay, and decremental conduction are explicitly enabled in the model.

The disclosed intracardiac simulation system models and emulates the electrical behavior of a patient's heart and transmits simulated intracardiac signals to an EP recording system. Advantageously, the system is capable of simulating complex cardiac rhythmic disorders for use in training scenarios. A training instructor accesses a simulator user interface to control the simulation system. The system delivers to the EP recording system simulated cardiac rhythm scenarios to which a trainee may respond. An EP recording system user interface serves as the access point for the trainee during the EP training session. Using the EP lab equipment, which is connected to the EP recording system, the trainee reacts to scenarios presented by the simulation system. Advantageously, the trainee's actions are in the clinical environment in which actual EP studies are conducted, thereby providing a realistic experience for the trainee. The EP recording system transmits to the simulation system the cardiac signals it has received and recorded. The simulation system compares the received cardiac signals (from the EP recording system) with the simulated cardiac signals that the simulation system transmitted to the EP recording system. If the two signals differ beyond a predetermined threshold, then the simulation system detects the presence of an artificial stimulation (e.g., a pacing pulse), delivered by, for example, the pulse generator in the EP lab environment. In such circumstances, the system modifies the simulation accordingly to reflect the delivered pacing stimulus.

Advantageously, various arrhythmias scenarios and therapeutic procedures may be simulated by the disclosed intracardiac simulation system. Illustratively, by way of non-limiting examples, the intracardiac simulation system may simulate, the following heart rhythm scenarios: normal sinus rhythm, sick sinus syndrome, sinoatrial exit block, first degree atrioventricular (AV) block, type I second degree AV block, type II second degree AV block, third degree AV block, dual AV node physiology, atrioventricular nodal reentry (AVNRT), atrioventricular reciprocating tachycardia (AVRT), to name a few. A cardiac stimulator may also be simulated according to certain embodiments of the present disclosure. Illustratively, by way of non-limiting examples, the disclosed intracardiac simulation system may simulate a pacer that paces in the high right atrium and/or in the right ventricle. The simulated stimulator may also sense simulated electrical activity in the high right atrium and/or in the right ventricle. The simulated stimulator may be configured to pace continuously or upon other, predefined circumstances. The simulated stimulator may also be configured to simulate anti-tachycardia pacing modalities and cardioversion therapeutic modalities (i.e., delivery of one or more high-voltage shocks to the heart to restore a normal rhythm to the heart) as well. In some embodiments, the disclosed intracardiac simulation system may simulate ablation of cardiac tissue. Illustratively, the simulated ablation, which is controlled by a user (i.e., an instructor) from the user workstation, is simulated by gradually increasing the refractory period of the target element (node or link) until it reaches a threshold. Once the threshold is reached, the refractory period is changed to infinity, thereby making the element incapable of being excited. In some embodiments, during simulated ablation, extra noise is added to the simulated intracardiac signals generated from the element being ablated to simulate the manner by which ablation is reflected on the EP recording system.

FIG. 1A is a simplified hardware block diagram of an EP study environment 100A including an embodiment of the disclosed intracardiac simulation system 102. The system 102 includes a simulation processor 104, a front end processor 108, a system interface 112, and a simulator user interface 118. The simulation processor 104 communicates with the front end processor 108 via connection 106 and with the simulator user interface 118 via connection 112. The front end processor 108 communicates with the system interface 112 via connection 110. An EP recording system 130 is included in the environment 100. The simulation system 102 communicates with the EP recording system 130 via connection 114. The EP recording system 130 communicates with an EP recording system user interface 134 via connection 132. Additional equipment may be used in the EP lab for training purposes, such as, for example, a pulse generator 136 and a pulse generator programmer 140. The pulse generator may be used to deliver pacing pulses to the cardiac simulation model in response to simulated cardiac rhythmic disorders that are being observed by the trainee during the EP training session. Additional equipment, not shown in FIG. 1A, may also be used for the training session. The connections 106, 110, 114, and 116 may be any form of electrical, optical, or wireless interconnect structures, known in the art, that are suitable to transport data, such as, by way of non-limiting example, ribbon cable, coaxial cable, twisted pair cables, Ethernet cables, Wi-Fi, Bluetooth, or ZigBee, to name a few.

The simulation processor 104 is configured, among other things, to execute an intracardiac model, calculate and transmit simulated cardiac signals, detect pacing signals, and communicate with a simulation instructor via the simulator user interface 118. The simulation processor 104 may be configured as a single-board computing system or as any other computing system capable of executing the various software components and controlling and/or communicating with the various hardware components described herein. In an embodiment, the simulation processor 104 is a general purpose computing system that may be configured as, by way of non-limiting example, a single-board computer such as a Raspberry Pi™ 2 Model B, offered by Raspberry Pi Foundation, United Kingdom, or a an Intel™ Edison Compute Module, offered by Intel Corporation of Santa Clara, Calif. USA, or the like.

The front end processor 108 includes signal conversion circuitry, signal conditioning circuitry, and pacing detection circuitry. The front end processor 108 may include multiple input/output bipolar channels. In one embodiment, the front end processor 108 includes six channels. However, the front end processor 108 may be configured to include any number of channels as required. Each bipolar output channel has a number, e.g., two, digital-to-analog converters (DACs) and e.g., two, analog-to-digital converters (ADCs). Simulated intracardiac signals are transmitted from the simulation processor 104 to the DACs of the front-end processor 108. The output signals of the DACs are conditioned, by the conditioning circuitry, to reduce the voltage level of the signals to expected values for intrinsic intracardiac signals (e.g., approximately 1-5 mV) and to change the output impedance (e.g., approximately 500Ω). Once transformed by the font end processor 108, the analog simulated intracardiac signals are transmitted, by way of the system interface 112, to the EP recording system 130. These signals, received by the EP recording system 130 represent the patient's cardiac electrical activity, and are treated as such by the EP recording system. The intracardiac signals received by the EP recording system 130 are directed back to the simulation processor 104, by way of the system interface 112, to the ADCs in the front end processor 108 where the output signals of the ADCs are conditioned to increase the voltage levels to expected values for the simulation processor 104 (e.g., approximately 1-5 V). In addition, the front end processor 108 includes circuitry necessary to detect pacing pulses and to transmit the results to the simulation processor 104. In some embodiments, the functionality of the front end processor 108 and the system interface 112 may be combined into a single physical unit.

Figure 1B:
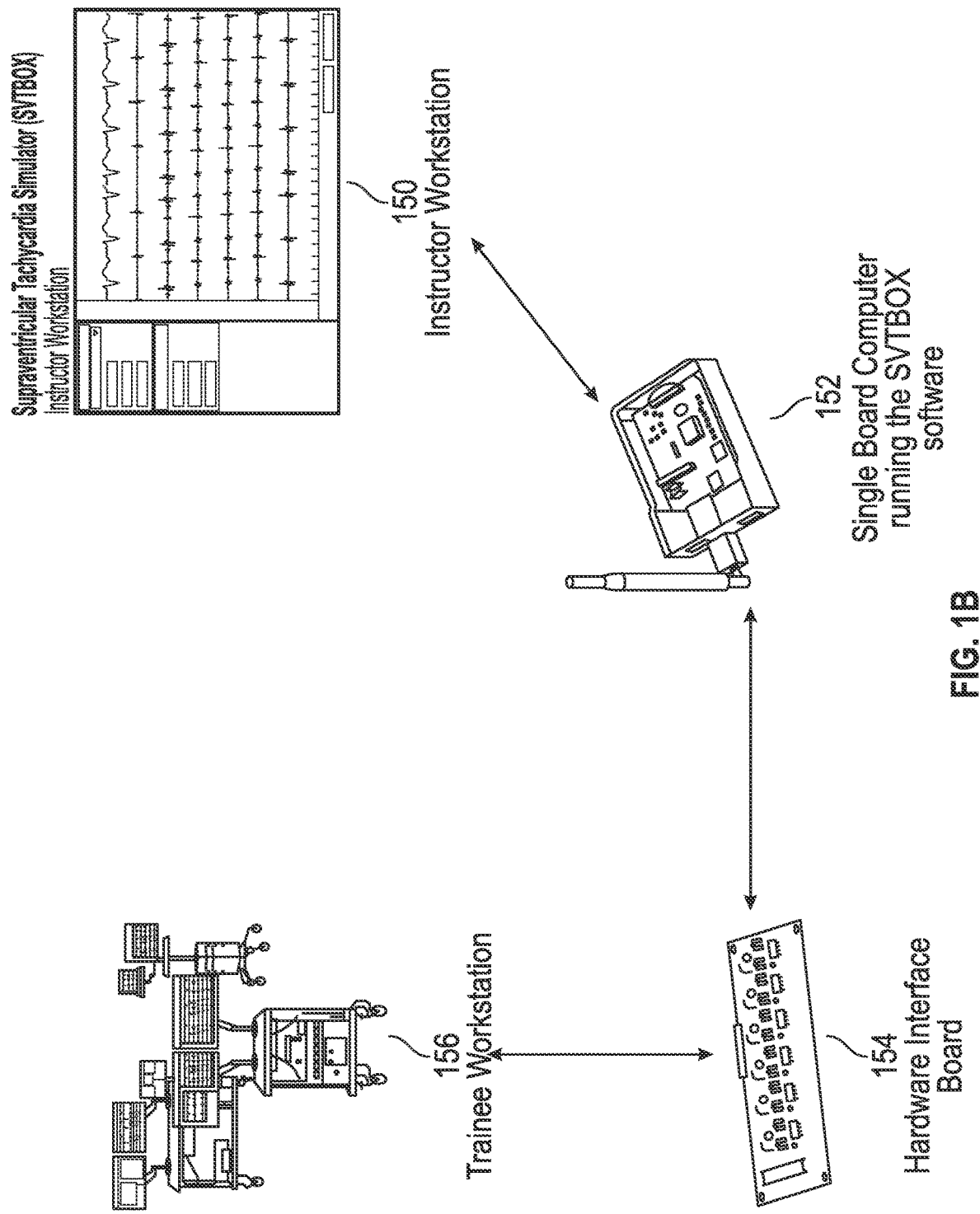
FIG. 1B is a general illustration of system components of an intracardiac simulation system according an embodiment of the present disclosure.

FIG. 1B is a general illustration of system components of an intracardiac simulation system according an embodiment of the present disclosure. An instructor workstation 150 includes a user interface display. The instructor workstation 150, which can be a personal computer, a tablet, or other such devices, communicates with a single board computer 152 via a wired or wireless link. The hardware interface board 154—which combines the functionality of a front end processor 108 and a system interface 112—is a special-purpose hardware component designed to generate low-noise, low amplitude signals that mimic actual human cardiac signals, and to sense stimulator pacing spikes. The hardware interface board 154 includes a set of channels. In one embodiment, the hardware interface board 154 includes six channels; however, the hardware interface board 154 may include any number of channels without departing from the scope of the present disclosure. Each channel includes a dual digital-to-analog converter with symmetrical, balanced voltage dividers to generate a low-noise, bipolar output signal based on the intracardiac model. The hardware interface board 154 also includes an analog-to-digital converter. The output of the analog-to-digital converter is transmitted to the software stimulator module 208, which then compares the received signal to the output signal generated by the intracardiac model. If the difference between the compared signals is greater than a predetermined threshold, then a pacing spike is detected, and the intracardiac model is informed to modify the model accordingly.

Figure 1C:
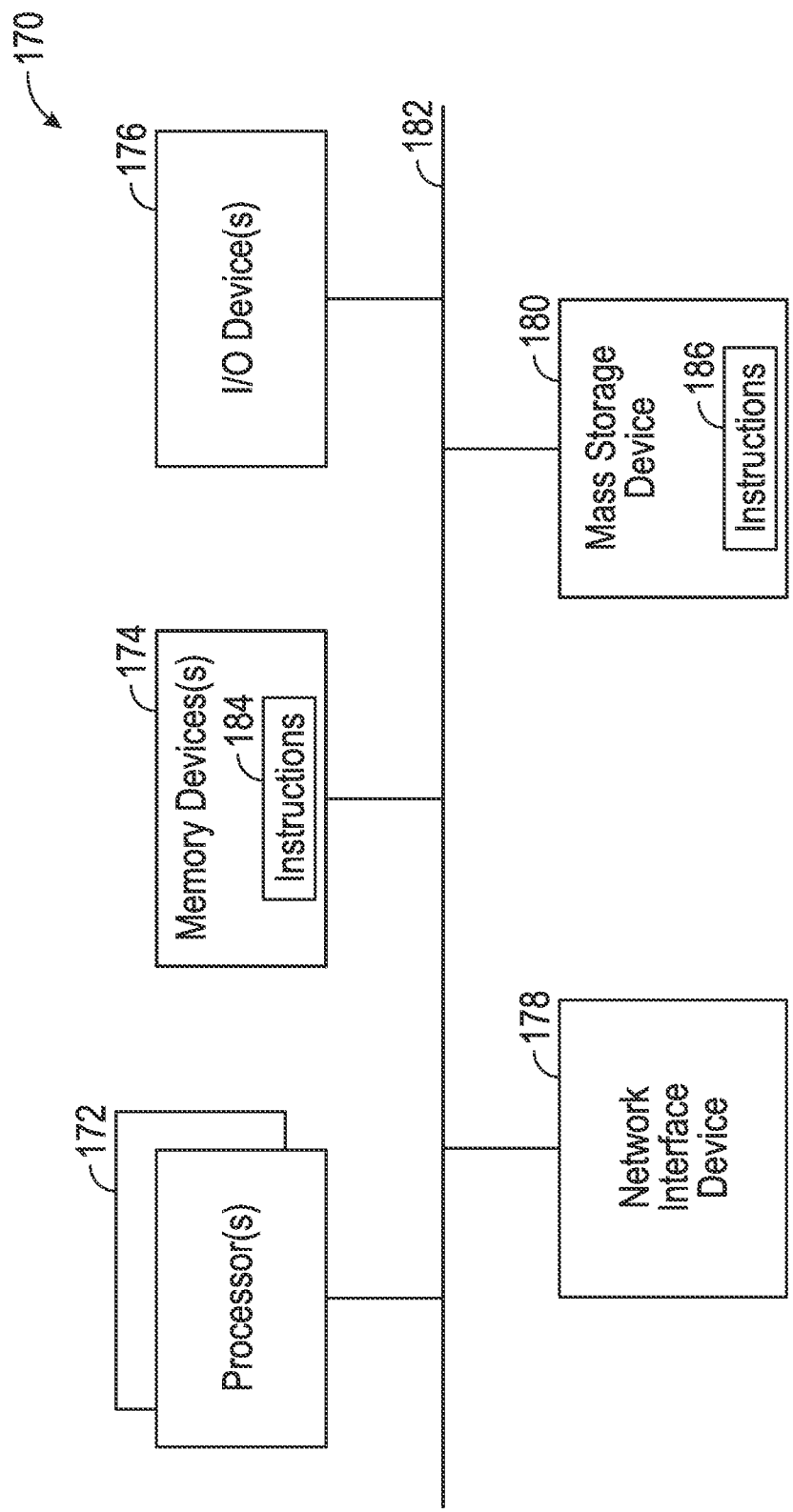
FIG. 1C is a functional block diagram of an example general purpose computing device and system suitable for use in executing the systems, methods and computer-readable media of the disclosed cardiac electrophysiology simulator.

FIG. 1C is a functional block diagram of an embodiment of a general purpose computing device and system 170 suitable for use in the simulation processor 104, the simulation user interface 118, the single board computer 152, and/or the instructor workstation 150. By way of illustration, the computing device 170 can include, for example, a single-board computer, a laptop computer, a stand-alone personal computer, and a server, to name a few. The computing device 170 can include one or more processors 172, one or more memory devices 174, one or more input and output (I/O) devices 176, one or more network interface devices 178, and a mass storage device 180. The one or more processors 172 can be configured to execute instructions and to process data to perform one or more functions, such as the methods and computer-readable media disclosed herein. The memory 174 can include one or more memory devices that store data, including without limitation, random access memory (RAM) and read-only memory (ROM). The I/O device(s) 176 may include one or more components that allow a user of the computing device 170 to interface with applications executing in the computing device 170. For example, the I/O device 176 may include devices such as, for example, a keyboard, a mouse, a touch pad, a touch screen, a microphone, an accelerometer, a camera, or any other user input device configurable to work with the computing device 170. The I/O device(s) 176 may also include, for example, a display (e.g., an LCD display, a CRT display, electronic ink, or a plasma display), a printer, a speaker, or any other output devices configurable to work with the computing device 170. The network interface device 178 may include any communication device for sending and receiving data across a network, including but not limited to, a network interface card, a modem or another network adapter capable of transmitting and receiving data over a network. The mass storage device 180 can include, for example, a magnetic storage device (e.g., a hard disk), an optical storage medium (e.g., a CD or DVD drive), a high-definition optical storage medium, an electronic storage device (e.g., EPROM or a flash drive), or other data storage devices known in the art. The components of the computing device 170 are coupled together by way of a bus 182, which may represent one or more buses. The memory device 174 and the mass storage device 180 may be employed to store a working copy and a permanent copy of programming instructions, illustrated as instructions 184 and 186, respectively, for implementing various aspects of the previously described embodiments of the present disclosure.

Figure 2:
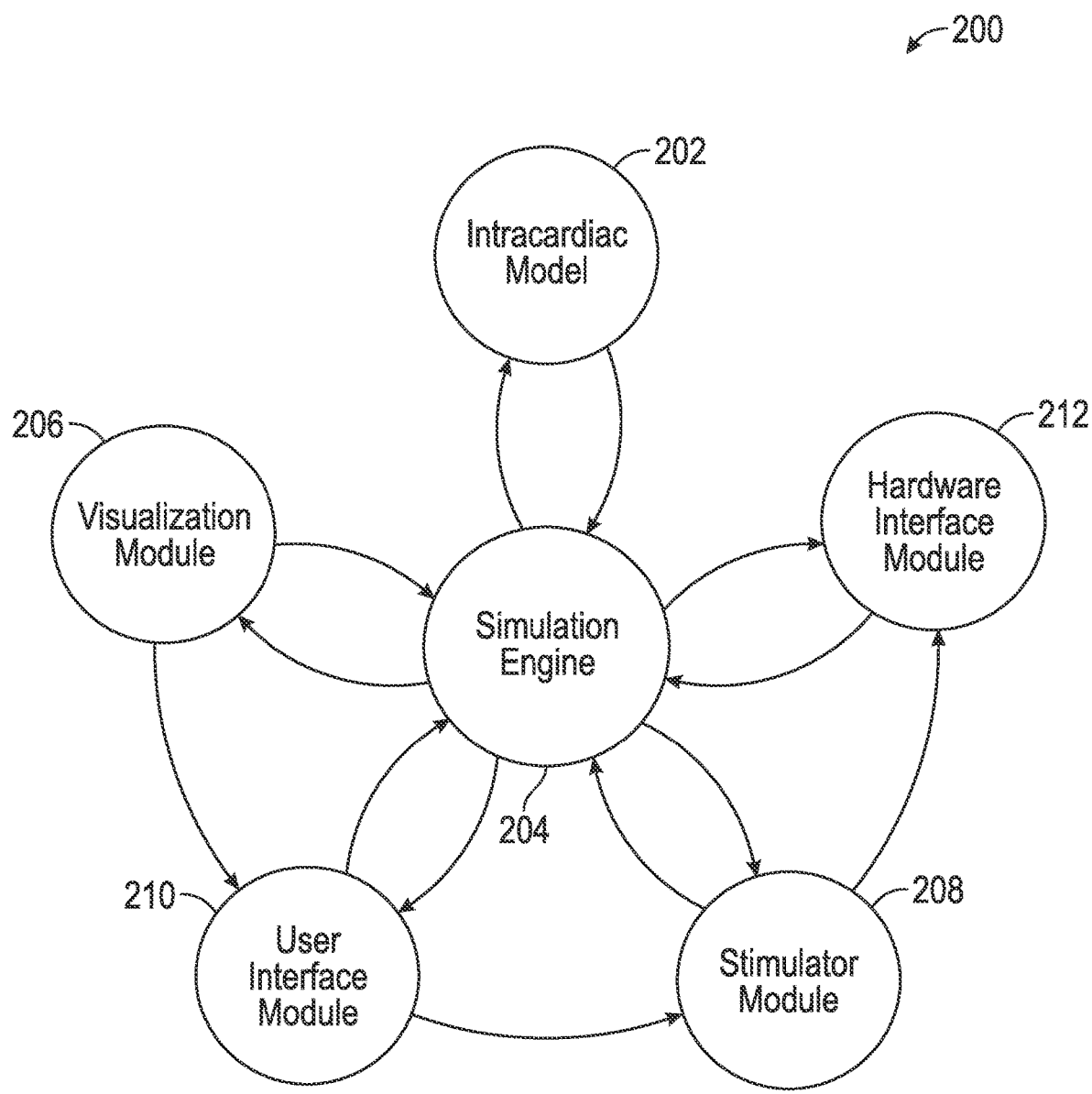
FIG. 2 is a simplified software block diagram of an intracardiac simulation system according an embodiment of the present disclosure.

FIG. 2 is a simplified block diagram of a software component structure 200 of an intracardiac simulation system 102 according an embodiment of the present disclosure. The software structure 200 includes an intracardiac module 202, a simulation engine 204, a visualization module 206, a stimulator module 208, a user interface module 210 and a hardware interface module 212, all of which are configured to be executed on the simulation processor 104.

The intracardiac model 202 is a graph-dynamical system. The topology of the system is defined in a model graph, G=(V, E), comprising nodes (V for vertices in the language of the graph theory) and links (E for edges). The nodes are points of electrophysiological interest, such as, for example, the sinus node, the atrioventricular (AV) node, and the right ventricular (RV) apex. Nodes are connected by links, which model the conduction system and pathways of the cardiac anatomy. Each link connects a pair of nodes and can be either unidirectional or bidirectional. Illustratively, the nodes, links and related modeling structures (such as, for example, timers, data, and the like) of the intracardiac model 202 may be implemented in software-controlled state machines. Examples of data derived, stored, and used by the intracardiac model 202 include, without limitation, the node cycle length (i.e., the duration of one cardiac cycle), the node diastolic interval (i.e., the duration of the refractory period of a cardiac cycle), the node refractory period, the link refractory period, and the link conduction delay.

Figure 3:
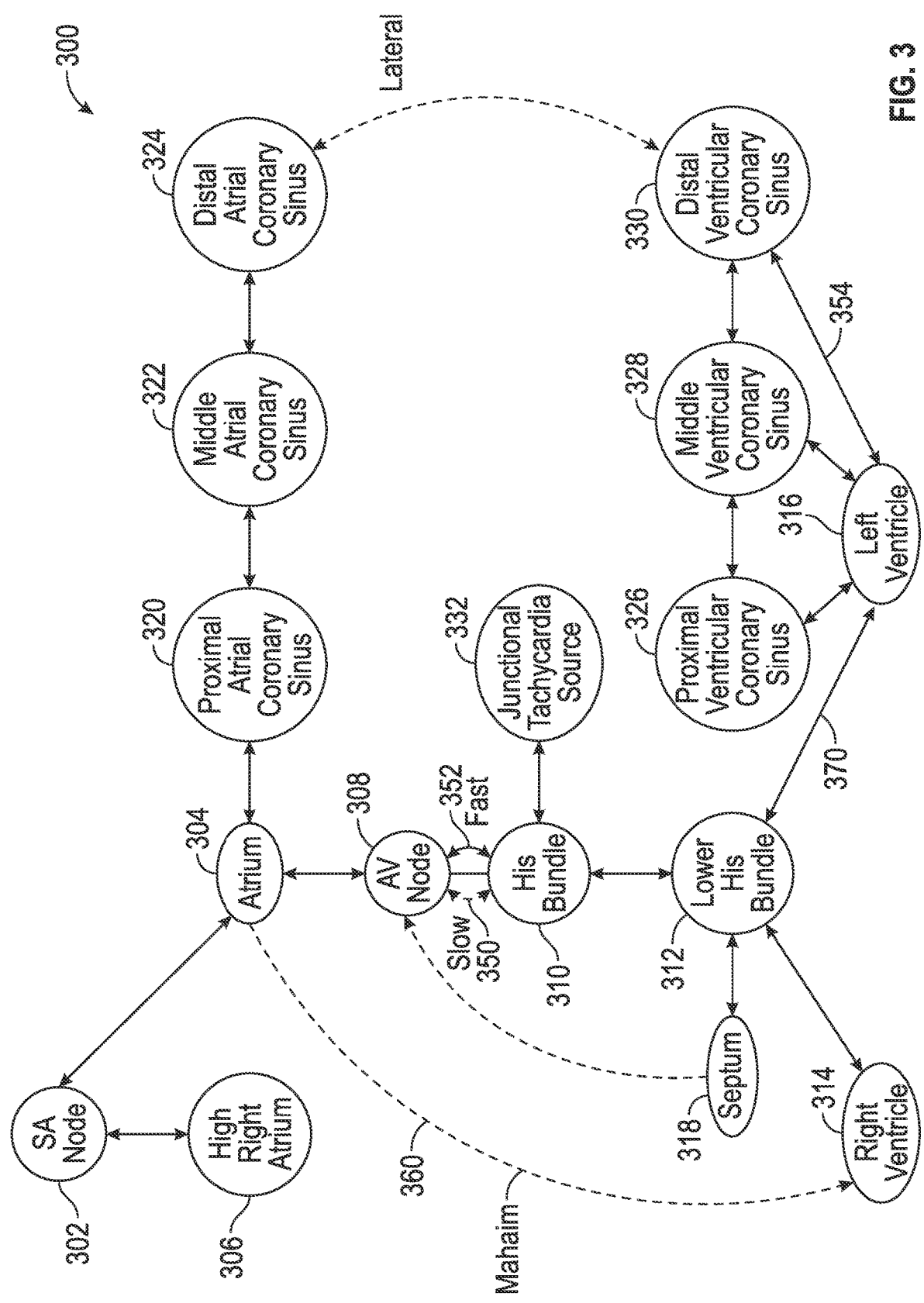
FIG. 3 is simplified block diagram of an intracardiac model according to an embodiment of the present disclosure.

FIG. 3 is a graph-based illustration of an embodiment of the intracardiac model 202 representing a cardiac conduction system. Nodes are labeled to represent structural portions or locations of the cardiac anatomy. The nodes depicted in FIG. 3 include the sinoatrial node 302, the atrium 304, the high right atrium 306, the atrioventricular node 308, the upper portion of the His bundle 310, the lower portion of the His bundle 312, the right ventricle 314, the left ventricle 316, the septum 318, the proximal atrial portion of coronary sinus 320, the middle atrial portion of the coronary sinus 322, the distal atrial portion of the coronary sinus 324, the proximal ventricular portion of coronary sinus 326, the middle ventricular portion of the coronary sinus 328, the distal ventricular portion of the coronary sinus 330, and a junctional tachycardia source 332. Links between nodes in the graph-based representation of FIG. 3 are depicted as lines between the nodes. As illustrated, some links are unidirectional while other links are bidirectional, and some links are depicted as being slower to conduct (illustrated as dotted lines). A unidirectional link pointing toward a node may be called an "incoming link" to that node because such a link provides an incoming stimulation signal to the node. A unidirectional link pointing away from a node may be called an "outgoing link" to that node because such a link provides an outgoing stimulation signal from the node. Thus, the structural components of the heart and the electrically-conductive paths between them can be modeled in this manner.

Figure 4A:
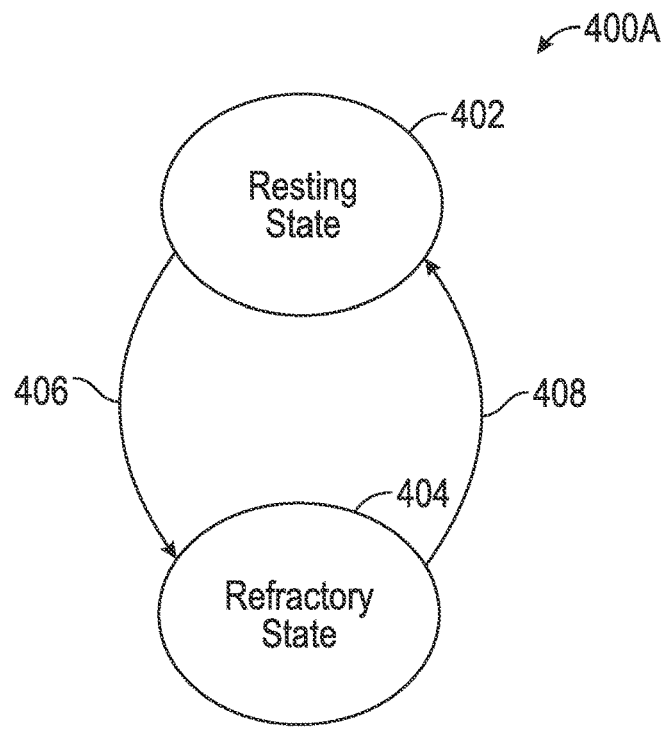
FIG. 4A is a simplified state diagram of a node used in an intracardiac model according to an embodiment of the present disclosure.

The dynamics of the system are determined by state machines having, among other things, nodes that represent structural portions or locations of the cardiac anatomy, links that represent conduction pathways between the nodes, timers assigned to the nodes and links, and memory for storing data associated with the state machine. The state of each node can be either in the resting or refractory state. A node is capable of being excited or stimulated when it is in the resting state. A node cannot be excited or stimulated when it is in the refractory state. Whenever a resting node is excited (i.e., receives a state transition signal), by either receipt of a pacing stimulation or through conduction from its immediate neighbor(s), the excitation causes the node's outgoing links to be stimulated, the node's state to change to refractory, and two timers: $\theta_1$ (corresponding to the node's refractory period) and $\theta_2$ (corresponding to the node's cycle length) to be recalculated and reset. After $\theta_1$ times out (i.e., the node's refractory period ends), the node reverts back to the resting state. A subset of the nodes are capable of automatically generating stimulations at specified intervals (i.e., the cycle length), which is controlled by $\theta_2$. These nodes comprise both physiological and artificial "pacemakers" that initiate an excitation wave. Such nodes include the sinus node, automatic foci, and external (user defined) stimulator sites, such as, for example, the right ventricular apex. FIG. 4A is a state diagram of a node 400A used in an intracardiac model according to an embodiment of the present disclosure. The node 400A transitions between a resting state 402 and a refractory state 404. Arrow 406 illustrates a transition from the resting state 402 to the refractory state 404, and arrow 408 illustrates a transition from the refractory state 404 to the resting state 402.

Figure 4B:
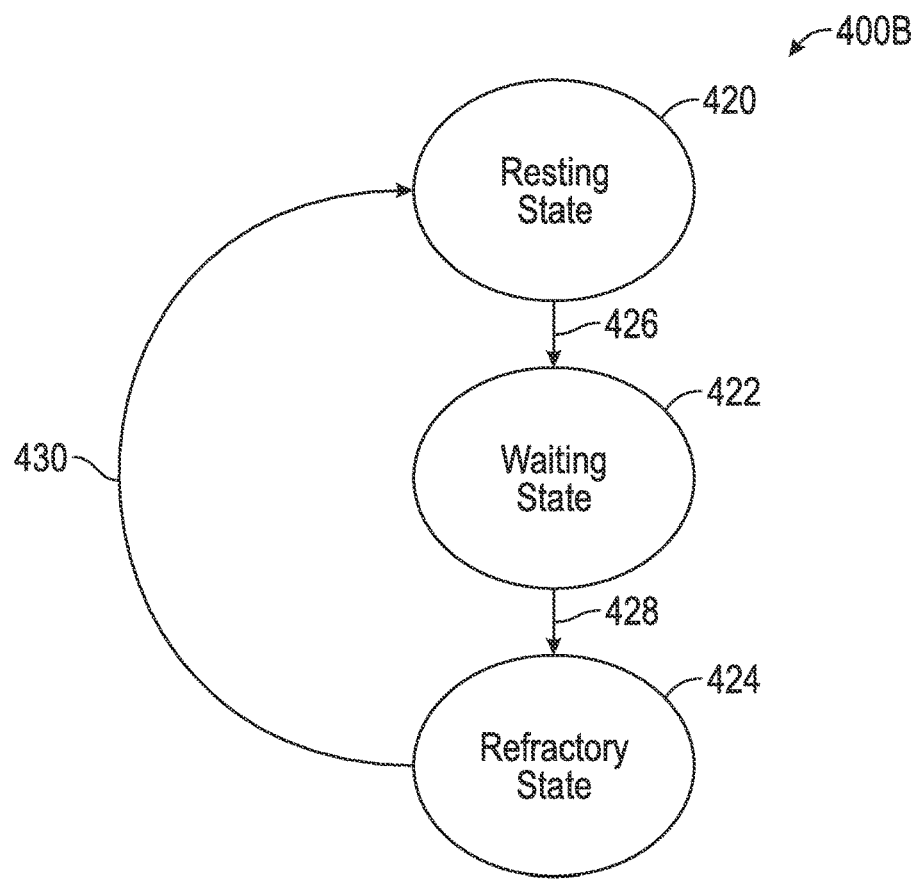
FIG. 4B is a simplified state diagram of a link used in an intracardiac model according to an embodiment of the present disclosure.

The possible states for links include resting, waiting, or refractory. Similar to the nodes, two timers are associated with each link: $\varphi_1$ (corresponding to the link's refractory period) and $\varphi_2$ (corresponding to the link's the conduction delay). Upon stimulation, a resting link changes state to waiting, dynamically recalculates the refractory period and waiting period (conduction delay), and resets timers $\varphi_1$ and $\varphi_2$. When the waiting period is over (i.e., the conduction delay ($\varphi_2$) times out), the link stimulates its outgoing node and changes its state to refractory. When the refractory period times out, the link reverts back to the resting state. FIG. 4B is a state diagram of a link 400B used in an intracardiac model according to an embodiment of the present disclosure. The link 400B transitions between a resting state 420, a waiting state 422, and a refractory state 424. Arrow 426 illustrates a transition from the resting state 420 to the waiting state 422. Arrow 428 illustrates a transition from the waiting state 422 to the refractory state 424, and arrow 430 illustrates a transition from the refractory state 424 to the resting state 420.

Advantageously, the disclosed intracardiac model 202 provides flexibility by dynamically recalculating waiting times, as governed by timers ($\theta_1$, $\theta_2$, $\varphi_1$ and $\varphi_2$), at the moment a node or link is excited, i.e., when a node transitions from the resting state to the refractory state, and when a link transitions from a resting state to a waiting state. Illustratively, according to an embodiment of the present disclosure, let n be a node which is stimulated at times . . . , $t_{k-2}$, $t_{k-1}$, $t_k$ and returns to the resting state at . . . , $t'_{k-2}$, $t'_{k-1}$, $t'_k$.

Let $T = t_k - t_{k-1}$ be the cycle length, and $D = t_k - t'_{k-1}$ be the diastolic interval at $t = t_k$. The simulation system updates the timers' waiting times, $W(\theta)$, for $\delta = \theta_1$ or $\theta = \theta_2$, in one of the following four ways:

1. $W(\theta) = w$, where w is a constant value. This is equivalent to the rigid models.
2. $W(\theta) = f(T; a, b, c, d)$, where T is the current cycle length, and where $f(x; a, b, c, d) = a + be^{-(x-c)/d}$ if $x > c$ and $a+b$ otherwise. Here, a, b, c, and d have constant values.
3. $W(\theta) = f(D; a, b, c, d)$, where D is the diastolic interval, and where $f(x; a, b, c, d) =$ is $a + be^{-(x-c)/d}$ if $x > c$ and $a+b$ otherwise. Here, a, b, c, and d have constant values.
4. $W(\theta) = g(p: x, y, z)$, where g is a stochastic (random) function that returns y if $p < x$ and z otherwise. By way of non-limiting example, p may be a uniform random variable in the range 0 to 1. The three parameters x, y, z may have constant values, or they may be dynamically determined by the functions $f(T; a, b, c, d)$ or $f(D; a, b, c, d)$, described above. Other random processes, including by way of non-limiting example, a uniform probability density function, a Gaussian probability density function, a Poisson distribution function, and a Laplace distribution function, may be used.

Use of the four above-described functions, or combinations of them, for $W(\theta)$, for $\theta = \theta_1$ or $\theta = \theta_2$ have been found to be sufficient to simulate most arrhythmias. However, the disclosed intracardiac model 202 allows and supports the use of other functions for $W(\theta)$, for $\theta = \theta_1$ or $\theta = \theta_2$.

Timers $\varphi_1$ and $\varphi_2$ of the links are updated similarly, in the following three ways:

1. $W(\varphi) = w$, where w is a constant value. This is equivalent to the rigid models.
2. $W(\varphi) = f(T; a, b, c, d)$, where T is the cycle length and where $f(x; a, b, c, d) = a + be^{-(x-c)/d}$ if $x > c$ and $a+b$ otherwise. Here, a, b, c, and d have constant values.
2. $W(\varphi) = f(D; a, b, c, d)$, where D is the diastolic interval and where $f(x; a, b, c, d) = a + be^{-(x-c)/d}$ if $x > c$ and $a+b$ otherwise. Here, a, b, c, and d have constant values.
3. $W(\varphi) = g(p: x, y, z)$, where g is a stochastic (random) function that returns y if $p < x$ and z otherwise. By way of non-limiting example, p may be a uniform random variable in the range 0 to 1. The three parameters x, y, z may have constant values, or they may be dynamically determined by the functions f(T; a, b, c, d) or f(D; a, b, c, d), described above. Other random processes, including by way of non-limiting example, a uniform probability density function, a Gaussian probability density function, a Poisson distribution function, and a Laplace distribution function, may be used.

Use of the above-described functions, or combinations of them, for $W(\varphi)$, for $\varphi=\varphi_1$ or $\varphi=\varphi_2$ have been found to be sufficient to simulate most arrhythmias. However, the disclosed intracardiac model 202 allows and supports the use of other functions for $W(\varphi)$, for $\varphi=\varphi_1$ or $\varphi=\varphi_2$.

As illustrated above, and in the examples provided below, use of an exponential decay function having a decay rate that depends, at least in part, on the cycle length and/or diastolic interval of the node is very useful in simulating certain electrical behaviors of the heart. Similarly, use of a random process, such as a uniform distribution function, may be very useful in simulating certain electrical behaviors of the heart. A skilled artisan will appreciate that numerous other functions and processes, random or otherwise, may be used to dynamically recalculate the waiting times $W(\theta)$ and $W(\varphi)$ without departing from the scope of the present disclosure.

Figure 9:
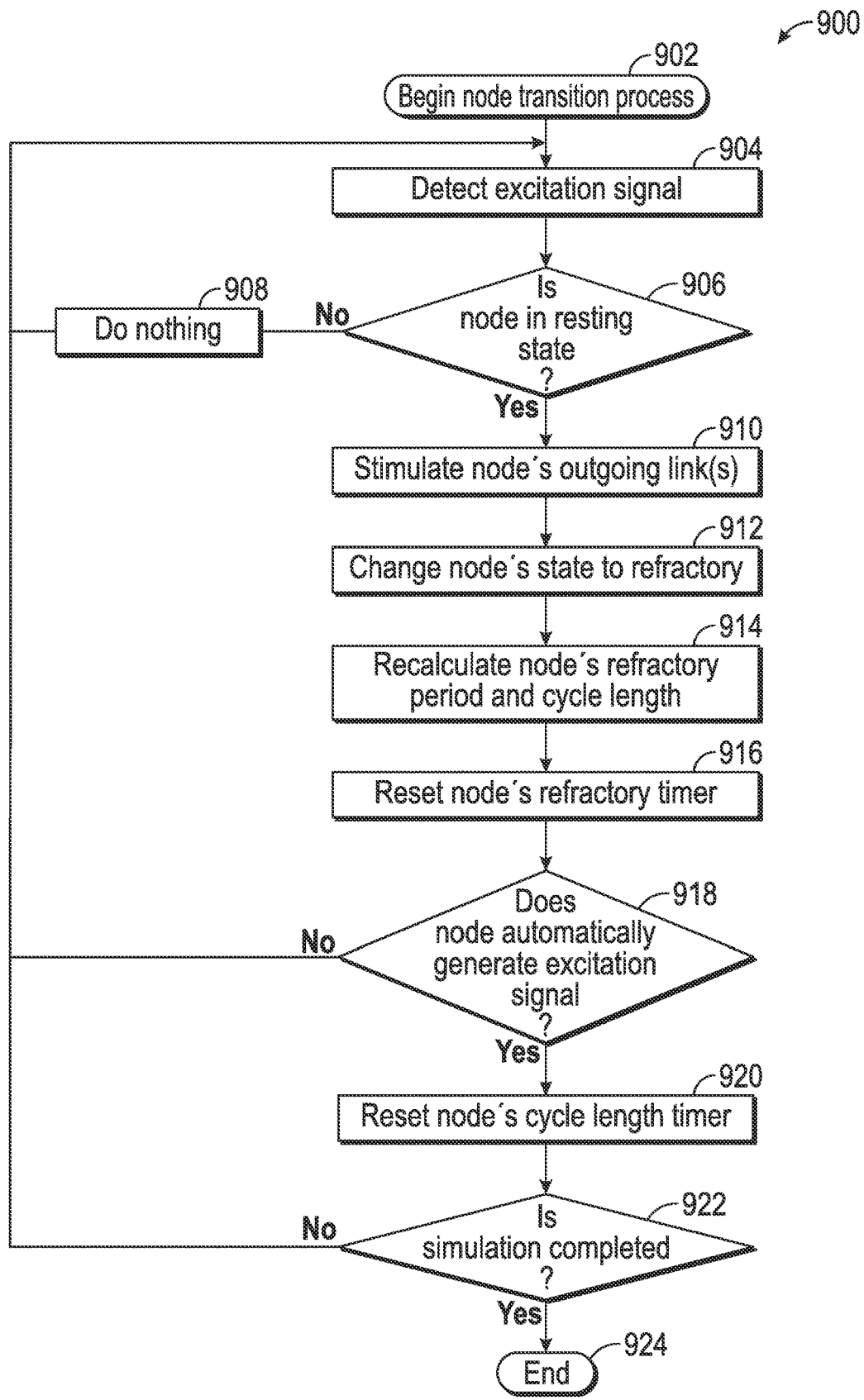
FIG. 9 is a flow diagram of a node transition process according to an embodiment of the present disclosure.

FIG. 9 is a flow diagram of a node transition process 900 according to an embodiment of the present disclosure. At block 902, the node transition process begins. At block 904, the process 900 receives a notification that an excitation or stimulation signal has arrived at the node. At block 906, the process 900 determines whether the node is in a resting state. A node may only be excited if it is in the resting state. Accordingly, if the node is not in the resting state, i.e., the node is in the refractory state, then the process 900 moves to block 908 and takes no action. The process 900 then advances back to block 904 to detect the next excitation signal. If the process 900 determines at block 906 that the node is in the resting state, then it advances to block 910 in which the process 900 transmits a stimulation (or excitation) signal to the node's outgoing links. At block 912, the node transitions to the refractory state. At block 914, the process 900 recalculates the node's refractory period and cycle length. As explained above, the intracardiac model 202 is capable of dynamically recalculating the node's refractory period and cycle length to as a function of the previous cycle length and/or the previous diastolic interval. This flexibility allows the system to realistically emulate physiological phenomena such as, for example, decremental conduction, rate-adaption of refractoriness, and paced suppression of automatic foci, among others, which are necessary for simulation of complex arrhythmias, such as, for example, tachycardias, which would not be feasible in a model configured with fixed/preset refractory periods. At block 916, the node's refractory period timer is reset with the recalculated refractory period. At block 918, the process 900 determines whether the node represents cardiac tissue that spontaneously generates electrical impulses (e.g., the sinus node, automatic foci, and external (user defined) stimulator sites, such as, for example, the right ventricular apex). If the node does not represent spontaneously stimulating cardiac tissue, then the process 900 returns to block 904 to detect the next excitation signal. If the node does represent spontaneously stimulating cardiac tissue, then the process 900 advances to block 920 and resets the nodes' cycle length timer with the recalculated cycle time. At block 922, the process 900 determines whether the simulation is completed. If not, the process 900 returns to block 904 to detect the next excitation signal. If the simulation is completed, then the process 900 ends at block 924.

Figure 10:
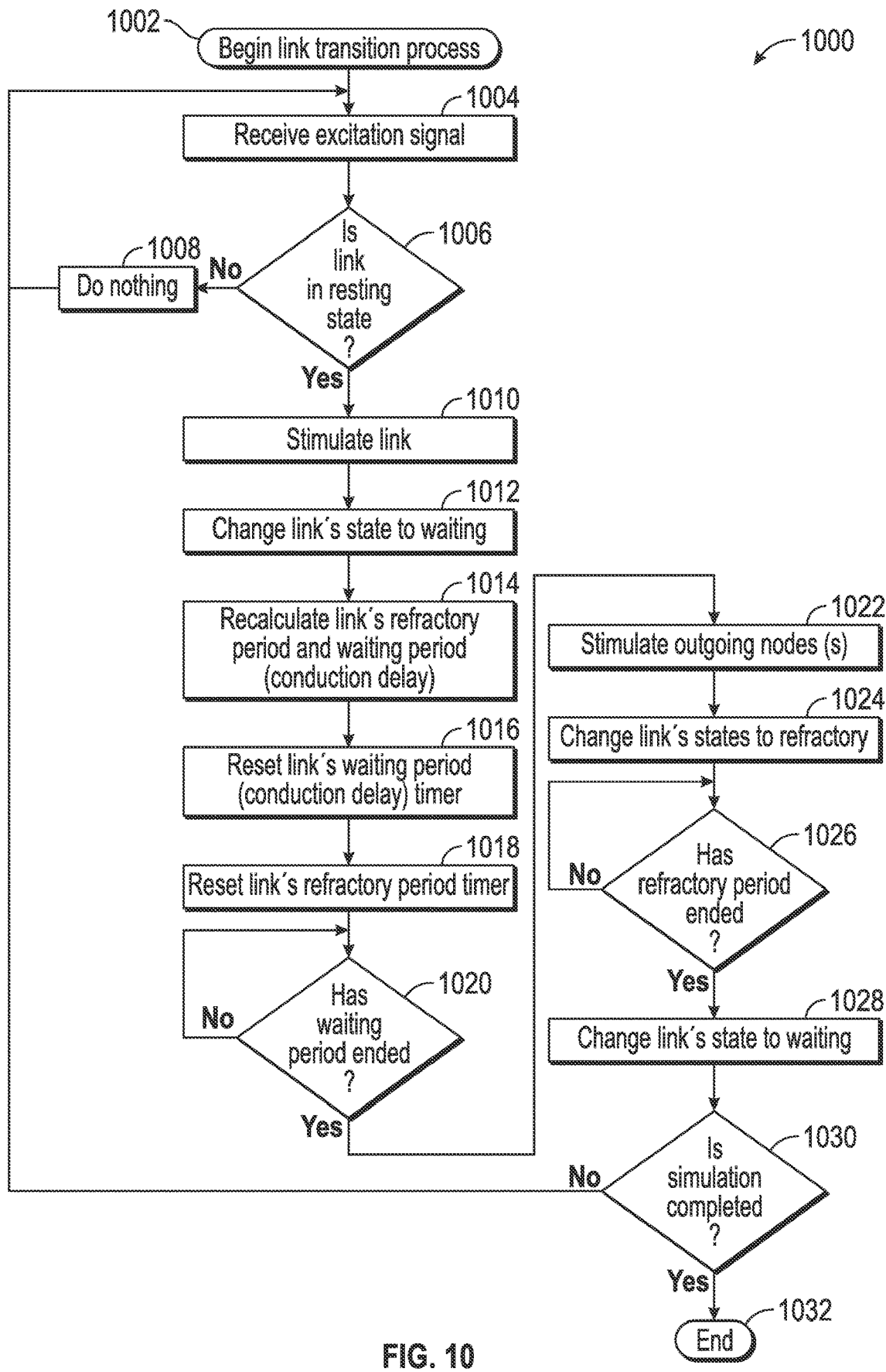
FIG. 10 is a flow diagram of a link transition process according to an embodiment of the present disclosure.

FIG. 10 is a flow diagram of a link transition process 1000 according to an embodiment of the present disclosure. At block 1002, the node transition process begins. At block 1004, the process 1000 receives a notification that an excitation or stimulation signal has arrived at the link. At block 1006, the process 1000 determines whether the link is in a resting state. A link may only be excited if it is in the resting state. Accordingly, if the link is not in the resting state, i.e., the link is in the waiting state or in the refractory state, the process 1000 moves to block 1008 and takes no action. The process 1000 then advances back to block 1004 to detect the next excitation signal. If the process 1000 determines at block 1006 that the link is in the resting state, then it advances to block 1010 in which the process 1000 transmits a stimulation (or excitation) signal to the link. At block 1012, the link transitions to the waiting state. At block 1014, the process 1000 recalculates the link's refractory period and conduction delay (i.e., waiting period). Advantageously, the ability to dynamically recalculate the link's refractory period and conduction delay as a function of the previous cycle length and/or the previous diastolic interval provides the capability to realistically emulate complex physiological cardiac arrhythmias. At block 1016, the link's waiting period timer is reset with the recalculated waiting period. At block 1018, the link's refractory period timer is reset with the recalculated refractory period. At block 1020, process 1000 waits until the waiting period has ended. Once the waiting period ends, the process 1000 advances to block 1022 and transmits a stimulation (excitation) signal to the outgoing node or nodes to which the link is connected. At block 1024, the link's state is changed to refractory. At block 1026, the process 1000 waits until the link's refractory period has ended. At block 1028, the link transitions to the waiting state. At block 1030, the process 1000 determines whether the simulation is completed. If not, the process 1000 returns to block 1004 to detect the next excitation signal. If the simulation is completed, then the process 1000 ends at block 1032.

The simulation engine 204 includes a software-based, real-time core that executes, among other things, the cardiac model 202. An example of an implementation of the simulation engine 204 is described in U.S. Pat. No. 7,039,893, entitled "System and Method for Implementing Configurable Finite State Machine," issued to DenBraber, the content of which is incorporated by reference herein in its entirety.

Figure 5:
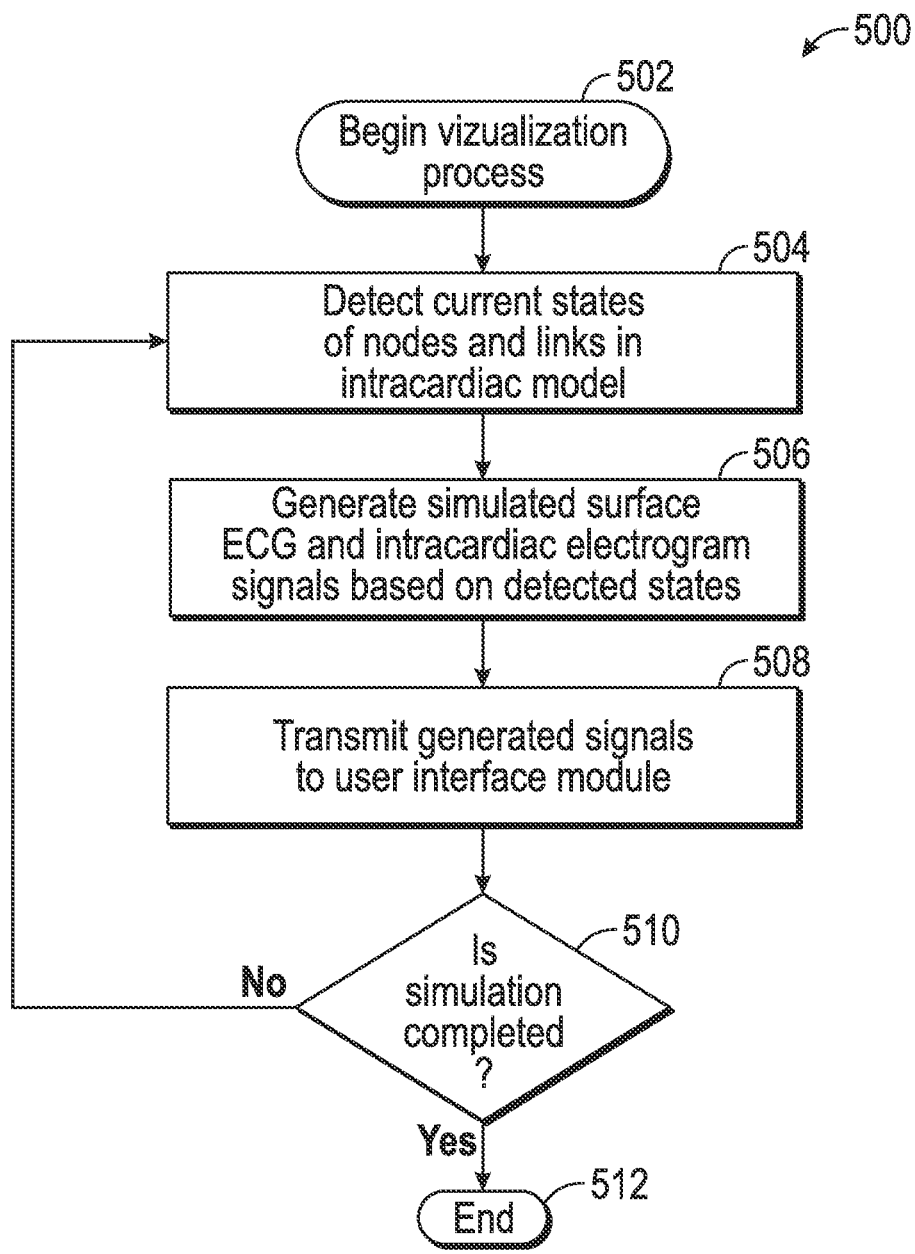
FIG. 5 is a flow diagram of a visualization process according to an embodiment of the present disclosure.

FIG. 5 is a flow diagram of a visualization process 500, as implemented by the visualization module 206, according to an embodiment of the present disclosure. The visualization process 500 causes simulated electrocardiogram signals to be displayed to the user. The process 500 begins at block 502. At block 504, the process 500 detects the current states of nodes and links implemented in the intracardiac model 202. At block 506, the process 500 generates simulated surface electrocardiogram (ECG) and intracardiac electrogram (IEGM) signals based on the detected states. At block 508, the process 500 transmits the generated electrocardiogram signals to the user interface module 210. At block 510, the process 500 determines whether the simulation is completed. If not, the process 500 returns to block 504 to detect the next states of nodes and links implemented in the intracardiac model 202. If the simulation is completed, then the process 500 ends at block 512.

Figure 6:
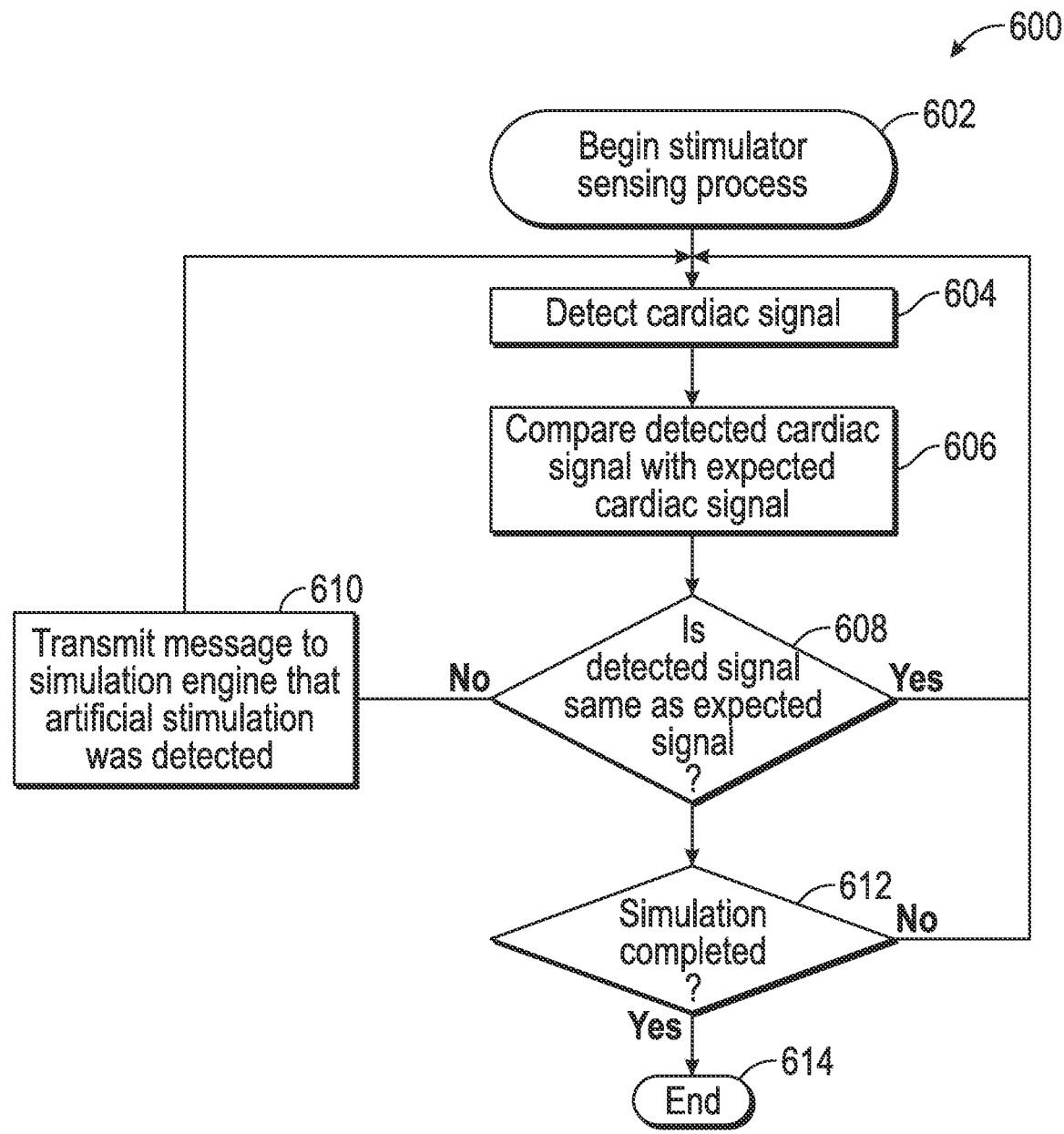
FIG. 6 is a flow diagram of a stimulator sensing process according to an embodiment of the present disclosure.

FIG. 6 is a flow diagram of a stimulator sensing process 600, as implemented by the stimulator module 208, according to an embodiment of the present disclosure. The process 600 begins at block 602. At block 604, the process 600 detects a cardiac signal transmitted from the EP recording system 130. At block 606, the process 600 compares the detected cardiac signal with an expected cardiac signal. The expected cardiac signal is the simulated cardiac signal that is generated by the intracardiac model 202 and transmitted to the EP recording system 130 via, for example, the front end processor 108 and the system interface 112. At block 608, the process 600 determines whether the detected cardiac signal is the same as the expected cardiac signal, within a predetermined threshold. If the two signals differ beyond the predetermined threshold, the process 600 advances to block 610. At block 610, the process 600 transmits a message to the simulation engine 204 that an artificial stimulation, such as a pacing pulse, has been detected. At block 612, the process 600 determines whether the simulation is completed. If not, the process 600 returns to block 604 to detect the next cardiac signal transmitted from the EP recording system 130. If the simulation is completed, then the process 600 ends at block 614.

Figure 7:
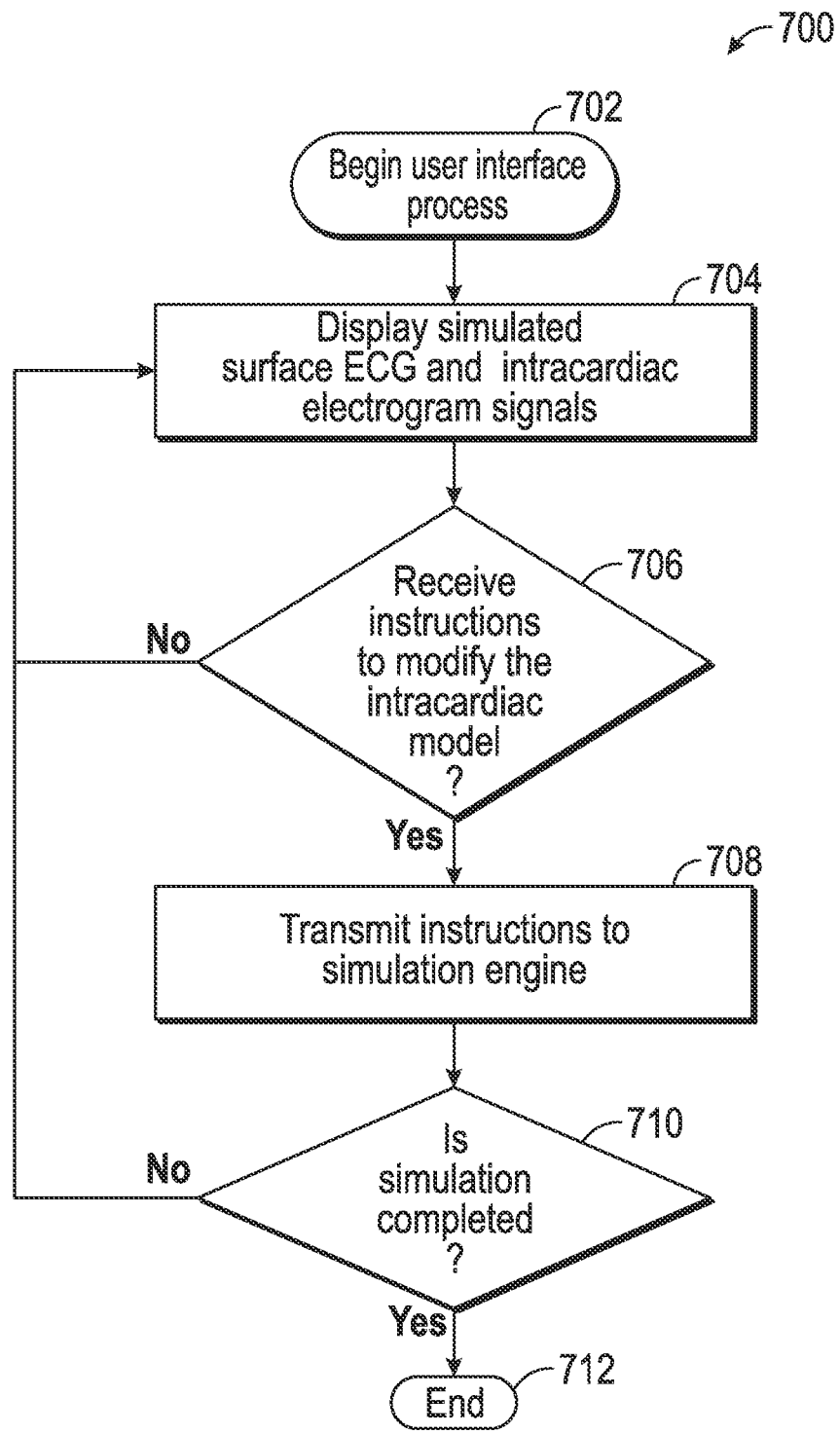
FIG. 7 is a flow diagram of a user interface process according to an embodiment of the present disclosure.
Figure 19:
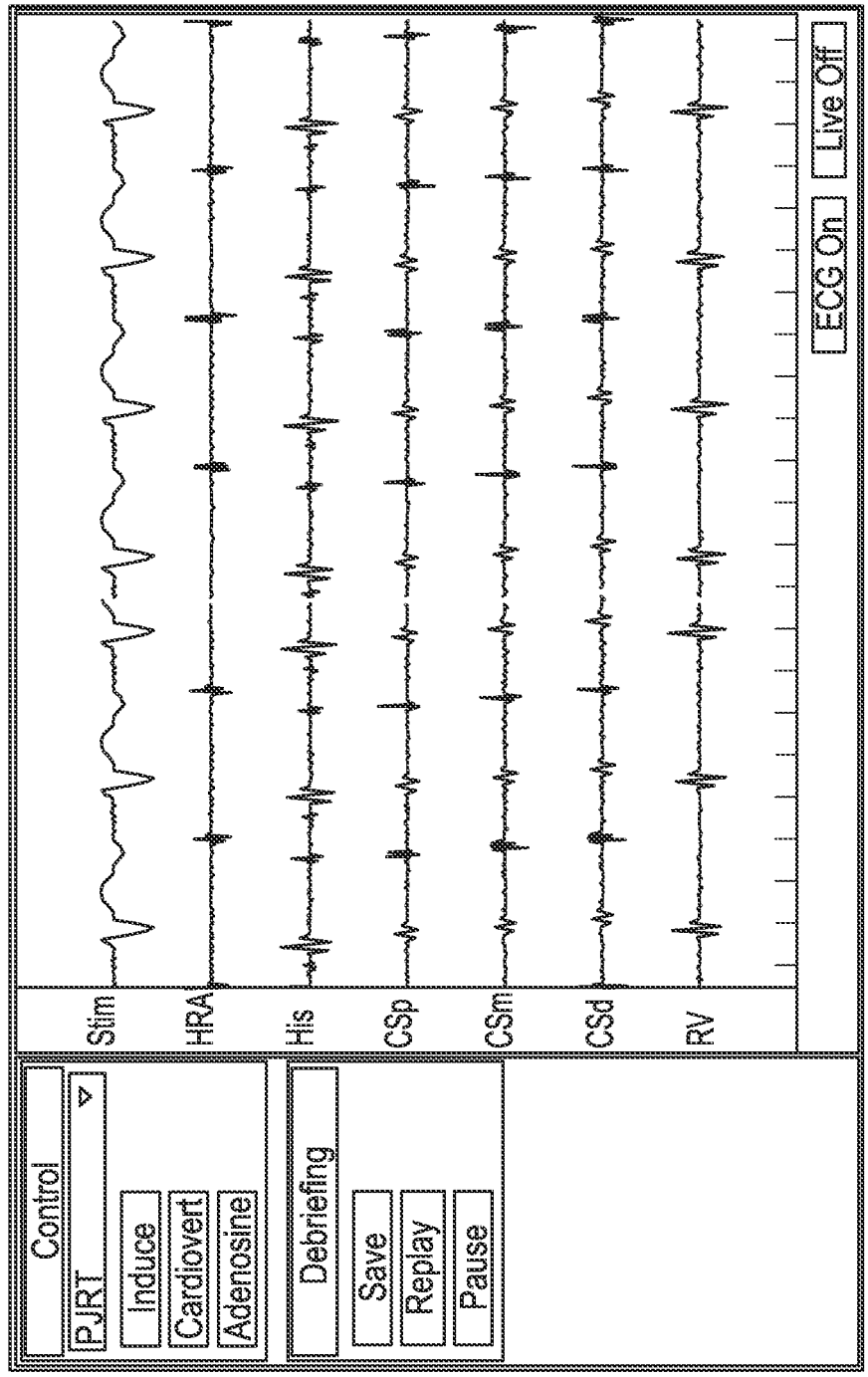
FIG. 19 is an example, web-based user display according to an embodiment of the present disclosure.

FIG. 7 is a flow diagram of a user interface process 700, as implemented by the user interface module 210, according to an embodiment of the present disclosure. The process 700 begins at block 702. At block 704 the process 700 causes to be displayed on the simulator user interface 118, simulated surface ECG and IEGM signals received from the visualization module 206 and as described above with respect to process 500. The user, typically an instructor, monitors the simulation as it progresses. FIG. 19 is an example of a user display presented on the simulator user interface 118. On the main screen of the display, a simulated surface ECG, labeled "Stim," is displayed. Additional simulated IEGMs are displayed corresponding to simulated intracardiac electrical activity in the high right atrium (HRA), the HIS bundle (His), the proximal, middle, and distal coronary sinus (CSp, CSm, and CSd, respectively), and the right ventricle (RV). Illustratively, movement of the simulated electrical cardiac signal may be seen as it propagates through the simulated nodes of the intracardiac model 202. The display also features a control panel with which the user (i.e., the EP Study instructor) may alter the behavior of the intracardiac model 202. For example the user may change the particular type of arrhythmia being simulated. Similarly, the user may simulate induction of an arrhythmia, cardioversion (i.e., deliver a defibrillation shock) of an arrhythmia, or administration of an anti-arrhythmia medication. The display of FIG. 19 also features a debriefing panel which permits the user to save, replay, and pause the display of the cardiac simulation. Referring back FIG. 7, at block 706, the process 700 determines whether it has received instructions to modify the intracardiac model 202. If not, the process 700 returns to block 704 to cause to be displayed the next simulated surface ECG and IEGM signals received from the visualization module 206. If instructions are detected, the process 700 advances to block 708 and transmits the received instructions to the simulation engine 204 to modify the intracardiac model 202. At block 710, the process 700 determines whether the simulation is completed. If not, the process 700 returns to block 704 to cause to be displayed the next simulated surface ECG and IEGM signals received from the visualization module 206. If the simulation is completed, then the process 700 ends at block 612.

Figure 8:
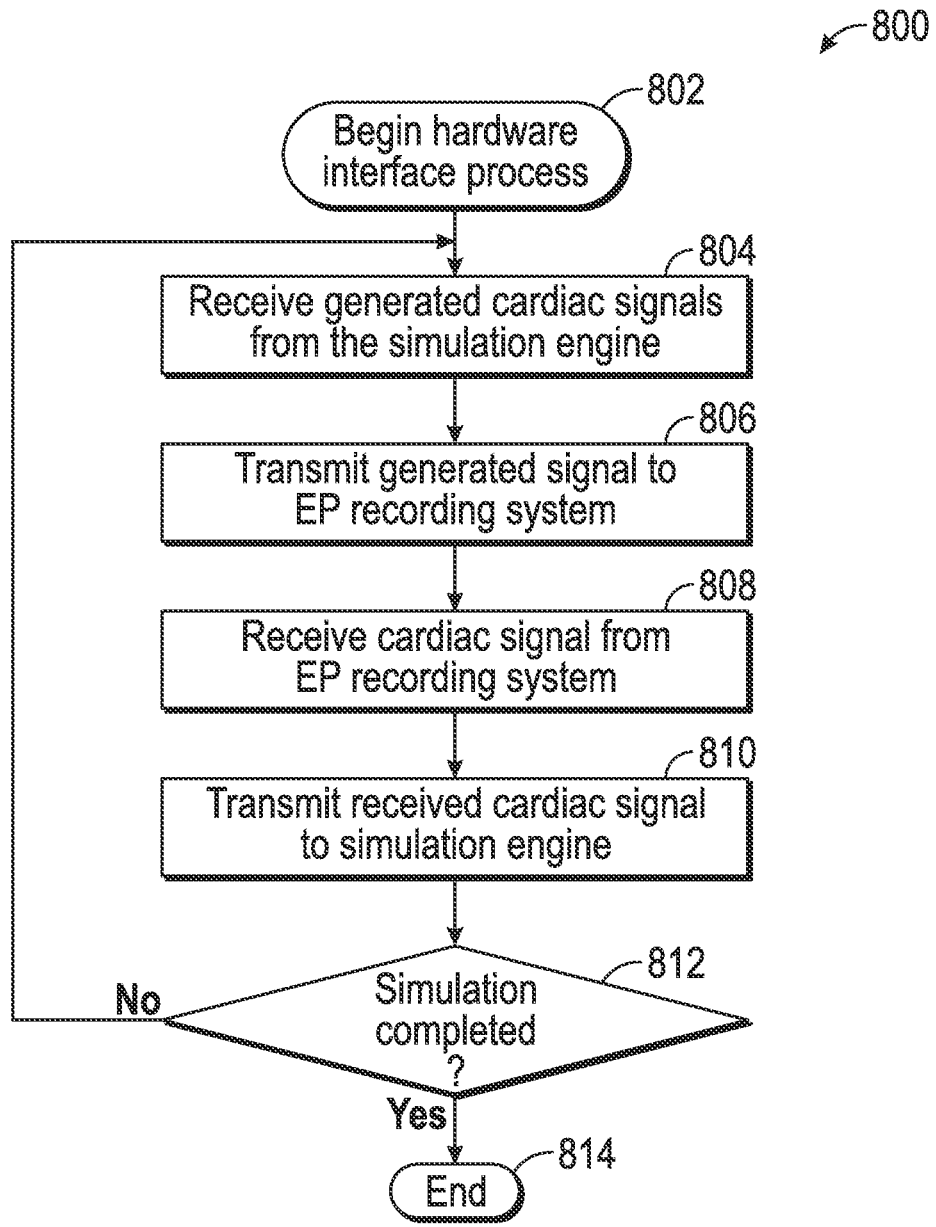
FIG. 8 is a flow diagram of a hardware interface process according to an embodiment of the present disclosure.

FIG. 8 is a flow diagram of a hardware interface process 800, as implemented by the hardware interface module 212, according to an embodiment of the present disclosure. The process 800 begins at block 802. At block 804, the process 800 receives a generated (and simulated) cardiac signal from the simulation engine 204. At block 806, the process 800 transmits the generated (and simulated) cardiac signal to the EP recording system 130. At block 808, the process receives, from the EP recording system 130, an EP system cardiac signal. At block 810, the process 800 transmits the received EP system cardiac signal to the simulation engine 204. At block 812, the process 800 determines whether the simulation is completed. If not, the process 800 returns to block 804 to receive the next generated (and simulated) cardiac signal from the simulation engine 204. If the simulation is completed, then the process 800 ends at block 814.

Advantageously, the two basic functions f and g, described above, are sufficiently general to allow for simulation of a wide range of realistic arrhythmias. Various abnormal scenarios can be generated by starting from a baseline scenario (e.g., normal sinus rhythm) and adding or modifying links. Provided below are non-limiting, illustrative examples of some arrhythmias which can be modeled by the disclosed intracardiac simulator, along with their responses to common pacing maneuvers.

Atrioventricular nodal reentrant tachycardia (AVNRT) is a prototypical reentrant arrhythmia and is important both clinically and for education. It is modeled by the addition of a slow pathway to the baseline model. The reentry circuit in AVNRT includes two links: the fast pathway and the slow pathway.

Figure 11A:
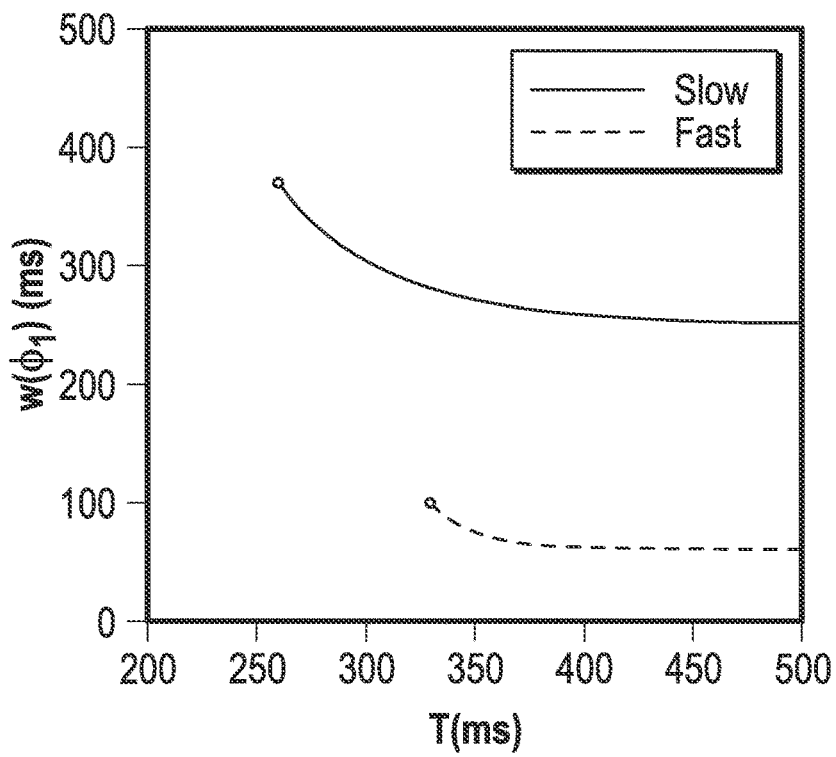
FIG. 11A is a graph of response curves of fast and slow atrioventricular nodal pathways according to an embodiment of the present disclosure.

For the fast pathway, we have:
$W(\varphi_1)=330$
$W(\varphi_2)=f(T: 330, 20, 40, 60)$
And for the slow pathway, we have:
$W(\varphi_1)=260$
$W(\varphi_2)=f(T: 260, 50, 120, 250)$ These values are chosen based on a typical clinical scenario. FIG. 11A depicts the calculated delay of each link, $W(\varphi_2)$, against the cycle length (T). The shorter the cycle length is, the longer the delay becomes, until the cycle length reaches a critical value (the refractory period) and blocks conduction. This is the essence of decremental conduction in cardiac tissue. By providing the ability to model such dynamic behavior of cardiac tissue, the present intracardiac simulation represents cardiac behavior realistically.

A similar response curve can be generated for the whole reentry circuit (loop) using the following formulas:

$$W(\phi_1) = \min W(\phi_1(i)), \text{ and}$$

$$W(\phi_2) = \sum_{i=1}^{n} W(\phi_2(i)),$$

where $\varphi_1(i)$ and $\varphi_2(i)$ refer to the ith link in the reentry loop composed of n links.

Figure 11B:
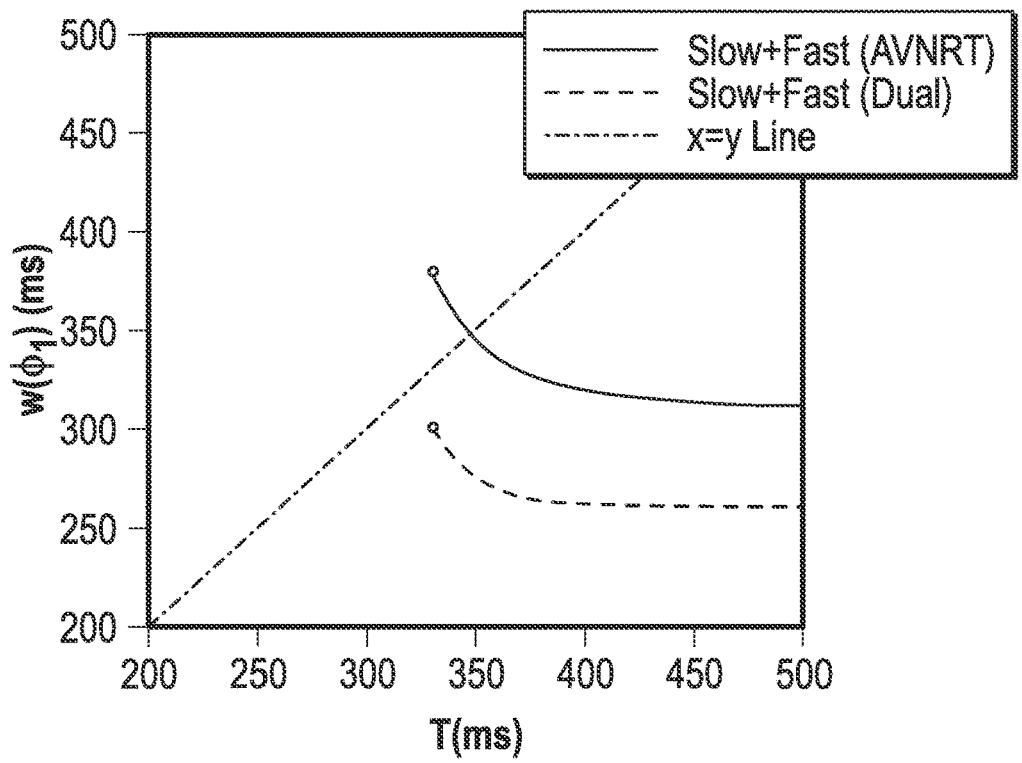
FIG. 11B is a graph of response curves of a reentry circuit in atrioventricular nodal reentry and a dual atrioventricular nodal scenario according to an embodiment of the present disclosure.

Referring back to AVNRT, we have:
$W(\varphi_1)=260$
$W(\varphi_2)=f(T: 330, 20, 40, 60)+f(T: 260, 50, 120, 250)$
FIG. 11B shows the response curve for the whole reentry loop.

Based on the non-linear dynamics principals, reentry is possible if this curve intersects the x=y line. As it is shown in FIG. 11B, this intersection is at T=342 ms, and this is the reentry cycle length of the induced AVNRT in this model.

Figure 11C:
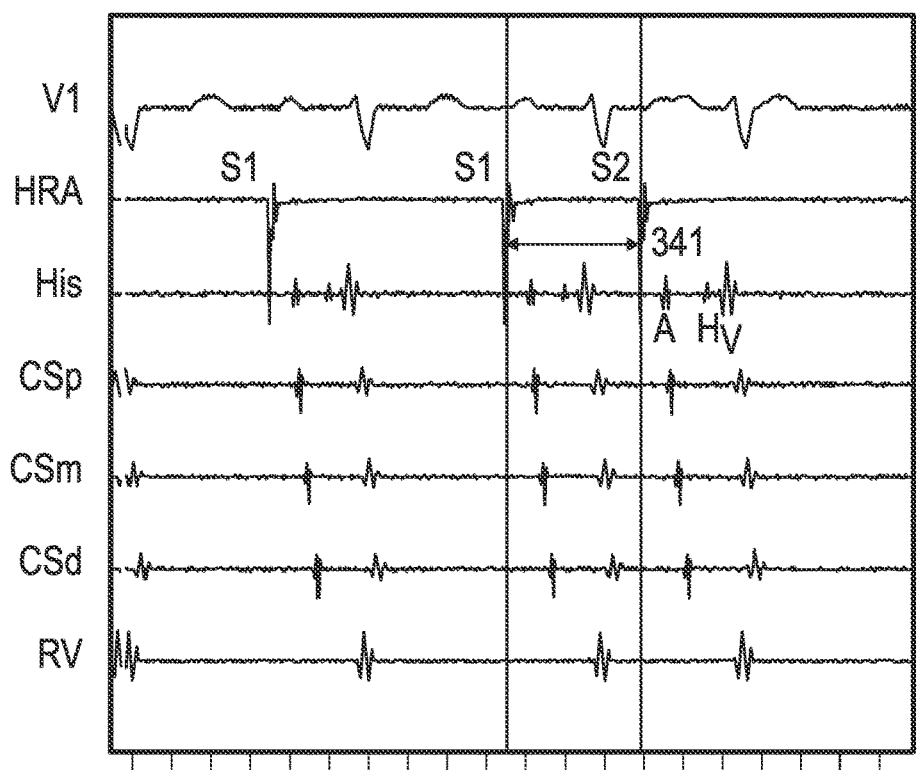
FIGS. 11C-D illustrate simulated surface and intracardiac signals in a dual atrioventricular nodal pathway scenario according to an embodiment of the present disclosure.
Figure 11D:
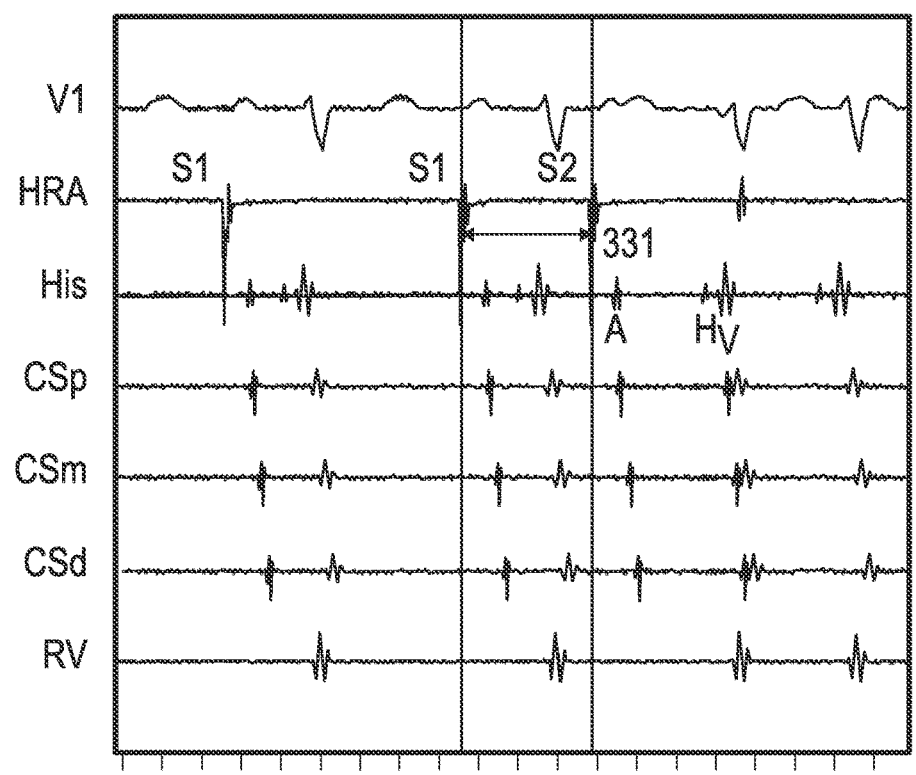

Now, the properties of the slow pathway are modified slightly to:
$W(\phi_1)=260$
$W(\phi_2)=f(T; 260,10,50,200)$
With this modification, we obtain the second curve that does not intersect the x=y line. Hence, reentry is not possible in this model. This is an example of dual AV nodal physiology without AVNRT. In this model, the refractory period of the slow pathway is set in such a way as to prevent sustained reentry. Delivery of extrastimuli with decremental coupling interval after a drive train demonstrates the presence of dual physiology with a jump in the AH interval, as illustrated in FIGS. 11C-D.

Figure 12A:
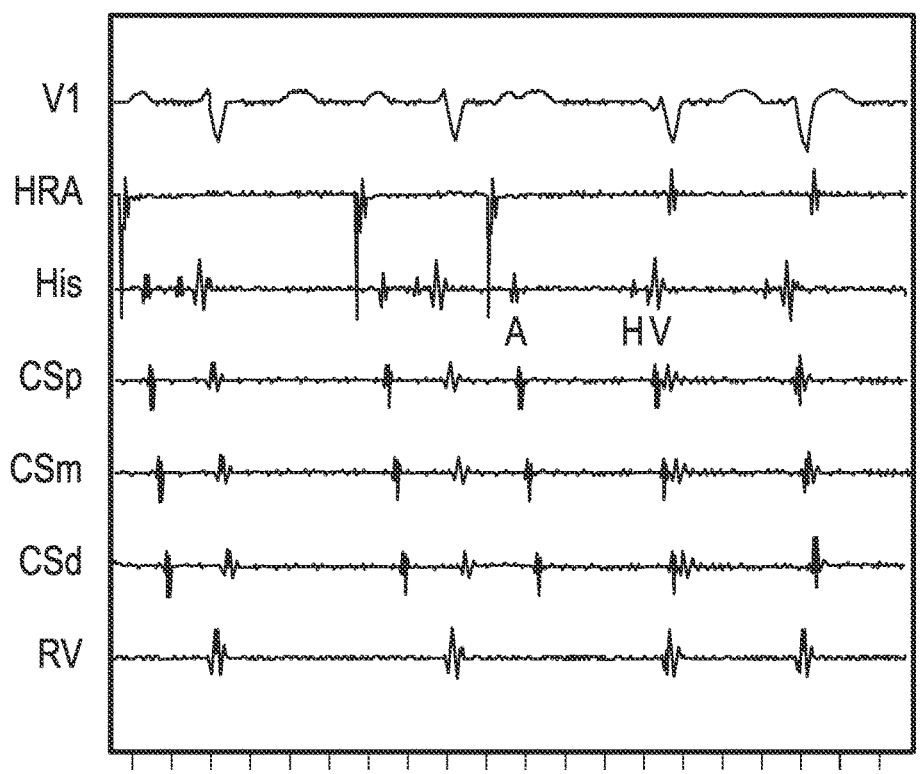
FIGS. 12A-D illustrate simulated surface and intracardiac signals in an atrioventricular nodal reentry (AVNRT) scenario, according to an embodiment of the present disclosure.
Figure 12B:
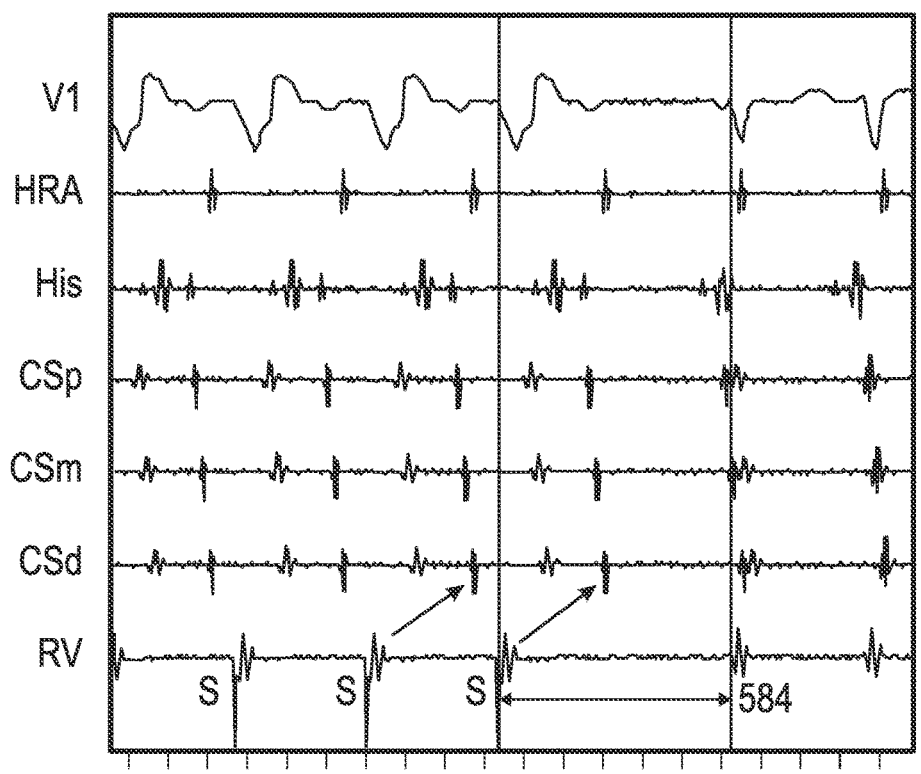
Figure 12C:
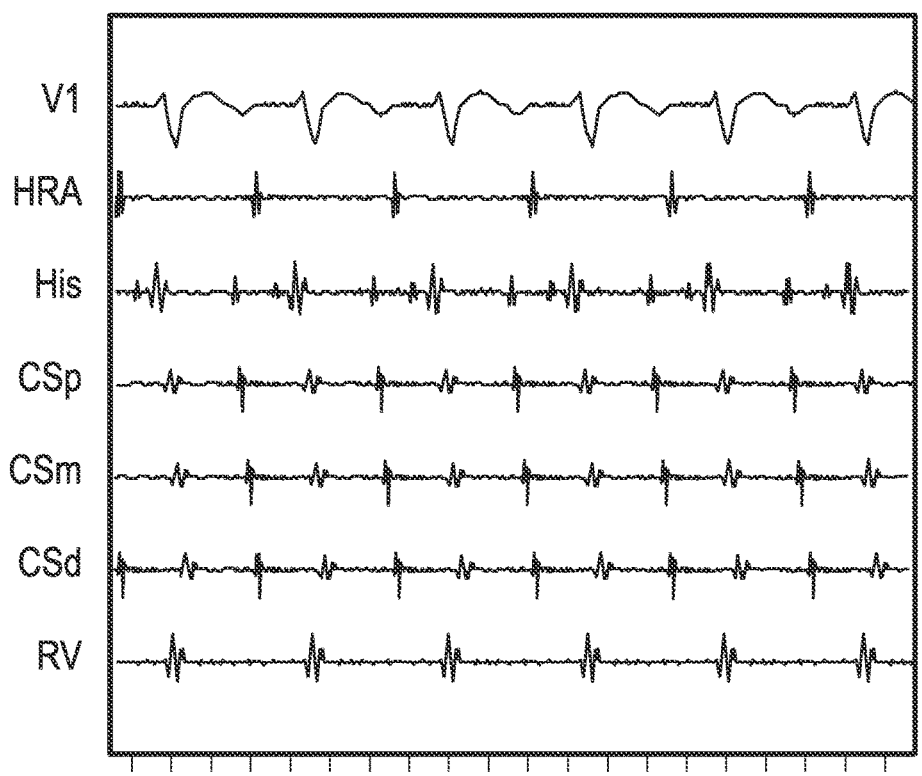
Figure 12D:
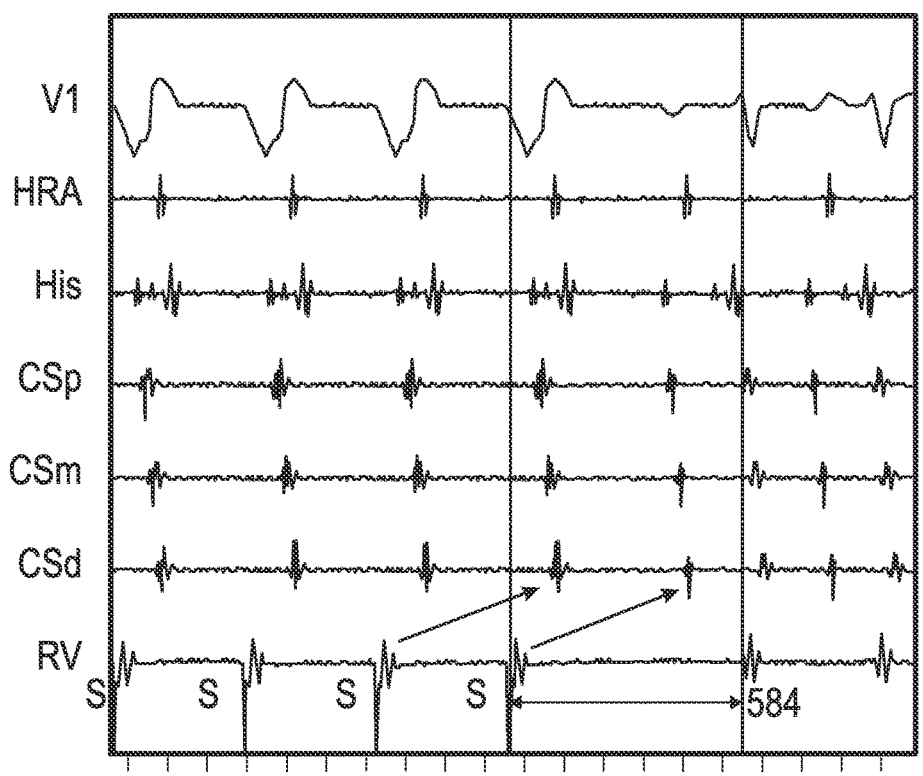

In contrast, in the AVNRT model, a timely atrial extrastimulus blocks in the fast pathway and initiates reentry, as illustrated in FIG. 12A. Ventricular overdrive pacing entrains the reentry with a VAV response, as illustrated in FIG. 12B, long post-pacing interval (PPI) and an increase in the VA timing ($\Delta VA>85$ ms), all consistent with typical AVNRT (slow-fast). On the other hand, delivery of ventricular extrastimuli to the same model initiates atypical AVNRT (fast-slow) with prolonged VA interval. Ventricular overdrive pacing, again, entrains the reentry with a long PPI and a pseudo VAAV response, as illustrated in FIGS. 12C and D.

Figure 13:
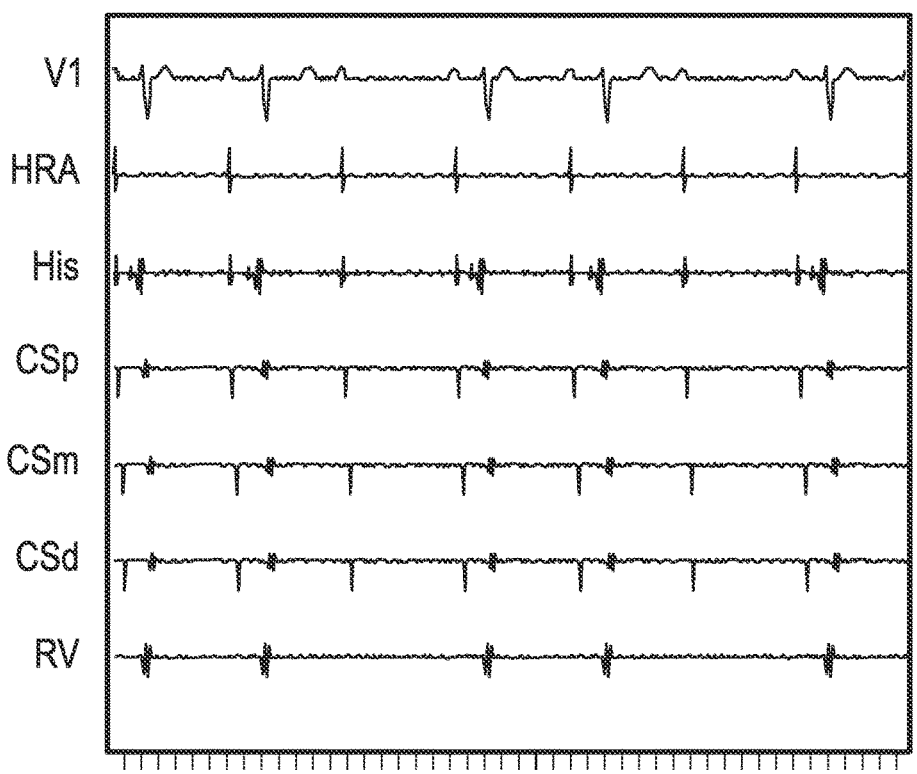
FIG. 13 illustrates simulated surface and intracardiac signals in a Type I, second-degree atrioventricular block scenario, according to an embodiment of the present disclosure.

Up to this point, we have used only the first two forms of W. We need to use the third form, with the diastolic interval as the independent variable instead of the cycle length, when the refractory period (i.e., $\varphi_1$) is also variable. For example, the type I second degree atrioventricular block (Wenckebach) is modeled by modifying the fast pathway to:
$W(\phi_1)=f(D; 100,50,200,600)$
$W(\phi_2)=f(D;100,20,40,80)$ Note that $D_k=t_k-t'_{k-1}=T-W(\phi_1(k-1))$, meaning the diastolic interval is the difference between the cycle length and the last refractory period. Now, assume the cycle length is T=750 ms. The baseline refractory period $W_0(\phi_1)=600$. Therefore, $D_1=T-W_0=750-600=150$ and $W_1=674$. and Similarly for the next beat, $D_2=T-W_1=750-674=76$ and $W_2=800$. But $T<W_2$, therefore the third beat blocks because the cycle length is less than the refractory period. The result is a 3:2 Wenckebach phenomenon at a cycle length 750 ms, as illustrated in FIG. 13.

Figure 14:
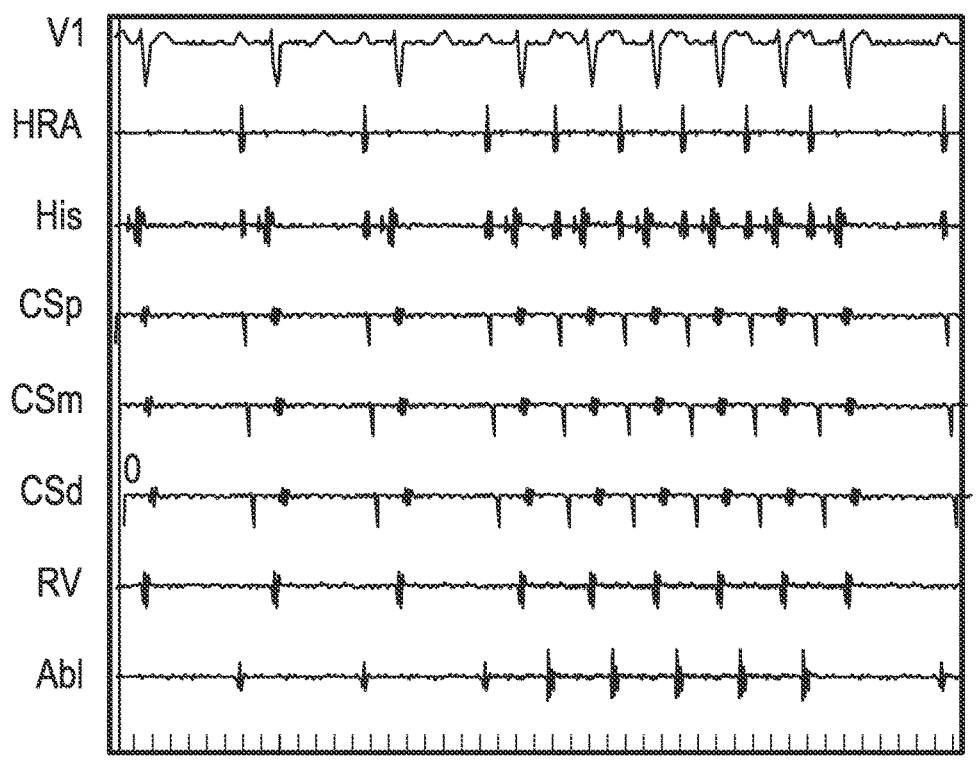
FIG. 14 illustrates simulated surface and intracardiac signals in an atrial tachycardia scenario, according to an embodiment of the present disclosure.

The fourth form of W is necessary to model automatic (non-reentrant) arrhythmias. For example, atrial tachycardia is modeled by adding a node with the following characteristics:
$\theta_1=200$
$\theta_2=g(f(T;350,150,0,0.99), 350,1000)$ An automatic focus fires randomly, but the probability of firing is dependent on the previous cycle length. This dependence of the probability of firing is encoded by having an "f" function instead of a constant as the first parameter to the "g" function. Therefore, the tachycardia focus fires in bursts instead of erratically, which is how an actual atrial tachycardia behaves. In addition, rapid pacing can induce firing, again as it is clinically expected. FIG. 14 illustrates this scenario.

Figure 15A:
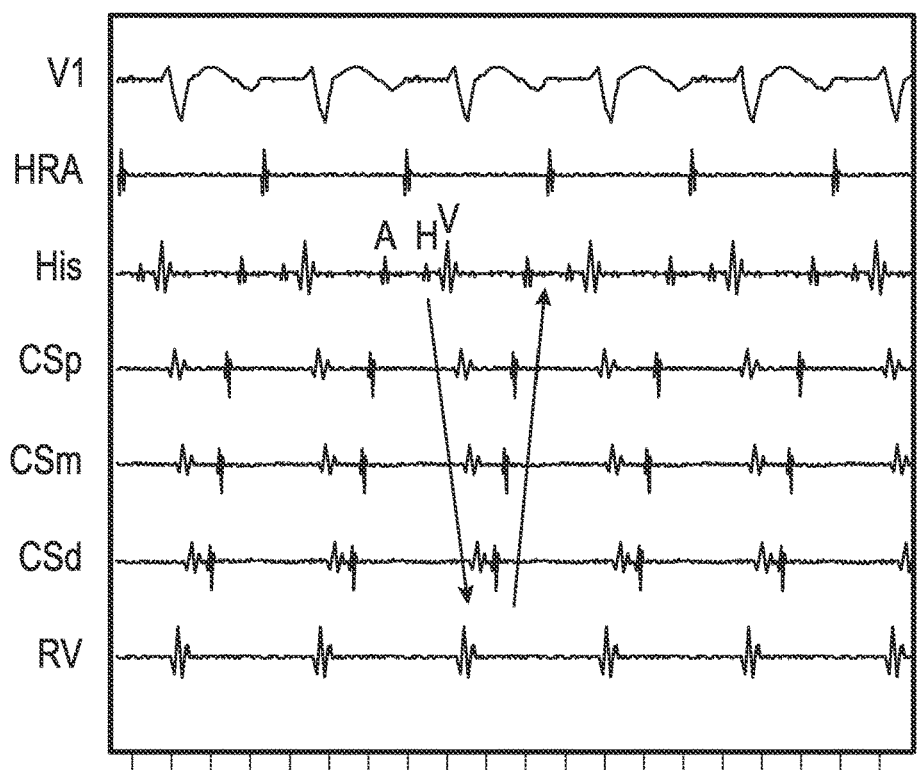
FIGS. 15A-B illustrate simulated surface and intracardiac signals in an atrioventricular reciprocating tachycardia (AVRT) scenario according to an embodiment of the present disclosure.
Figure 15B:

Accessory pathways are modeled as links between atria and ventricles. Addition of a link between distal coronary sinus and adjacent ventricle creates the substrate for atrioventricular reentrant tachycardia (AVRT). Both unidirectional (concealed) and bidirectional (manifest) accessory pathways are implemented. The parameters for a manifest lateral accessory pathway are:
$W(\phi_1)=150$
$W(\phi_2)=80$
and for the concealed pathway (unidirectional) are:
$W(\phi_1)=150$
$W(\phi_2)=f(T;310,50,40,40)$ The reentry analysis is similar to the one for AVNRT, except the circuit (reentry loop) is longer and is composed of seven links. FIGS. 15A and B show an episode of orthodromic reciprocating tachycardia (ORT) using a concealed pathway. Ventricular overdrive pacing entrains the tachycardia with relatively short PPI and ($\Delta VA<85$ ms).

Figure 16:
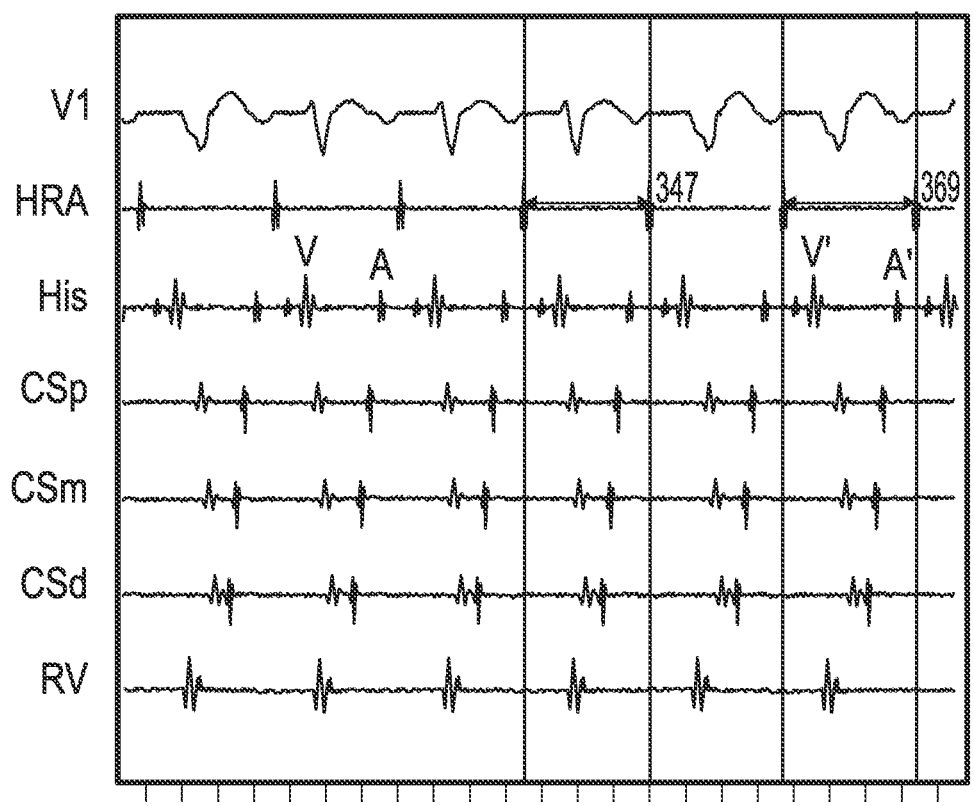
FIG. 16 illustrates simulated surface and intracardiac signals in an AVRT scenario exhibiting the "Coumel's sign" according to an embodiment of the present disclosure.

FIG. 16 depicts an example of the "Coumel's Sign," where the prolongation of the VA interval (and usually the tachycardia cycle length) after spontaneous bundle branch block during ORT proves the existence and participation of an accessory pathway ipsilateral to the blocked bundle.

Figure 17A:
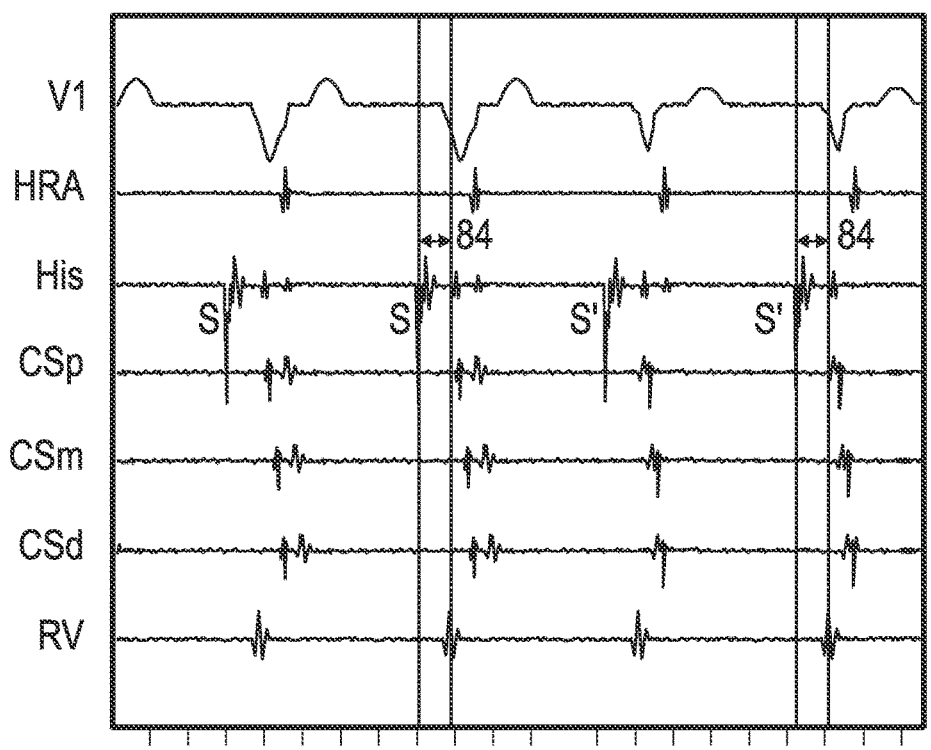
FIGS. 17A-B illustrate simulated surface and intracardiac signals during para-Hisian pacing according to an embodiment of the present disclosure.
Figure 17B:
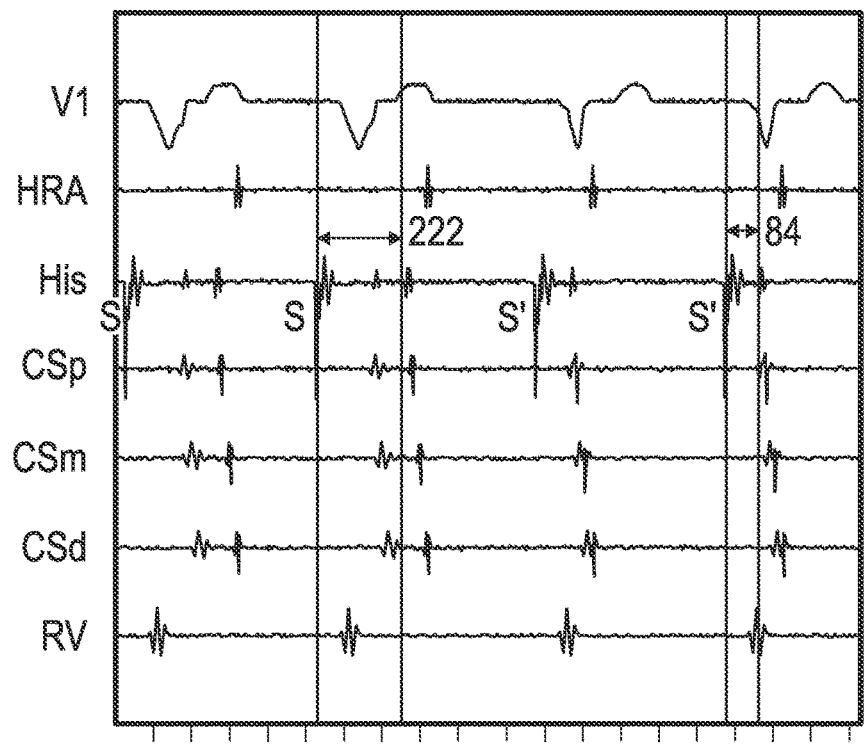

Septal pathways can be particularly difficult to diagnose. The parameters for a septal pathway are:
$W(\phi_1)=200$
$W(\phi_2)=f(T;250,100,60,80)$ Multiple pacing maneuvers are developed to distinguish a septal pathway from AVNRT. In the presence of a non-decremental septal pathway, there is no significant difference in the VA timing during either high-amplitude para-Hisian pacing (capturing both local ventricular tissue and the His bundle) or low-amplitude para-Hisian pacing (capturing only the local tissue) (FIG. 17A). On the other hand, if the only connection between the ventricle and atria is through the AV node, high-amplitude pacing results in a shorter VA timing (FIG. 17B).

Figure 18A:
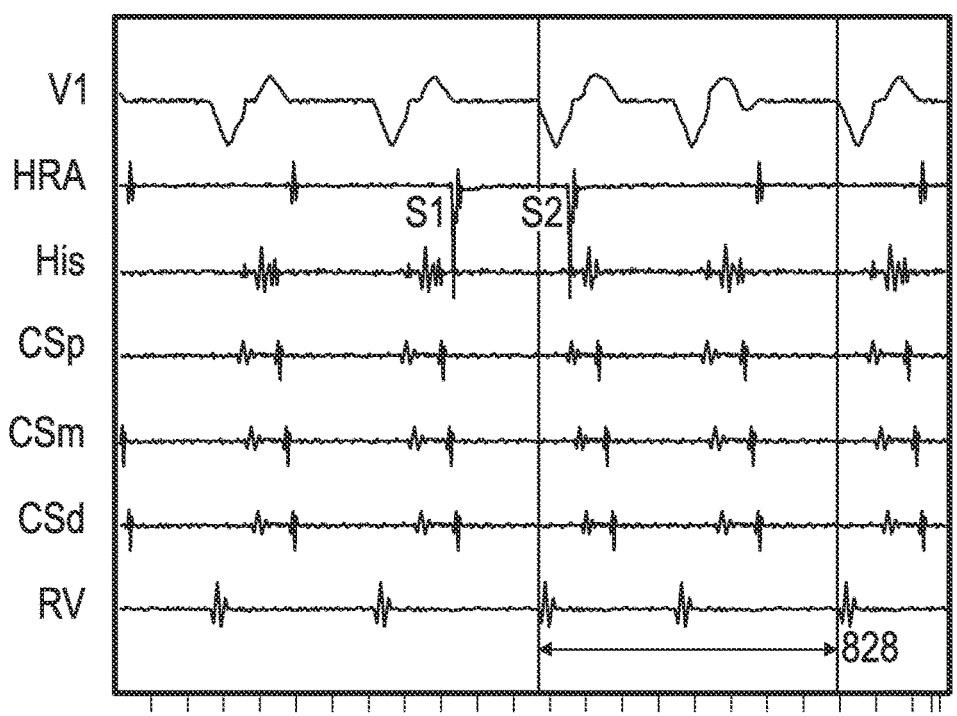
FIGS. 18A-B illustrate simulated surface and intracardiac signals during wide complex tachycardia (WCT) according to an embodiment of the present disclosure.
Figure 18B:
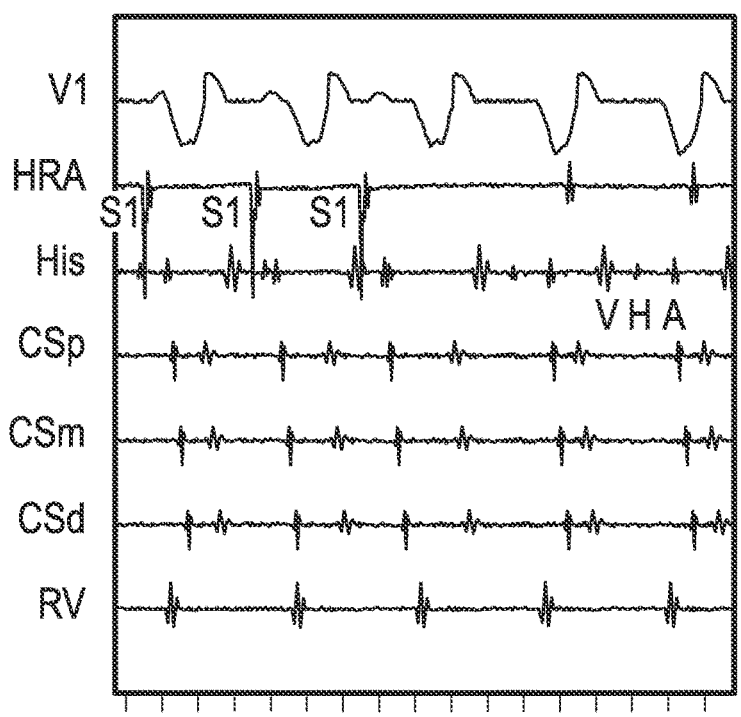

Wide complex tachycardia (WCT) can also pose a difficult diagnostic challenge. Here, we look at two different WCT and their response to atrial pacing. We model atriofascicular pathways (Mahaim fibers) by adding a decremental unidirectional link between the atrium and RV apex:
$W(\phi_1)=270$
$W(\phi_2)=f(T;270,50,100,250)$ Atrial extrastimuli initiates an antedromic reciprocating tachycardia (ART) using the accessory pathway with a left bundle branch block (LBBB) morphology. A His refractory atrial premature beat that advances the next ventricular complex and resets the tachycardia proves that the accessory pathway participates in tachycardia (FIG. 18A). Another WCT with LBBB morphology is the Bundle Branch Reentrant (BBR) tachycardia, which is modeled by adjusting the refractoriness of the link between His and LV (i.e. the left bundle). The reentry circuit is composed of the right bundle, transseptal conduction, and retrograde conduction through the left bundle. Atrial overdrive pacing dissociates the atrial activity from the ventricles (FIG. 18B), which is highly suggestive of ventricular tachycardia.

Thus, systems, apparatuses, and methods directed to an interactive, intracardiac signal simulator that emulates the electrical behavior of a patient's heart have been disclosed herein. Various other modifications, adaptations, and alternative designs are of course possible in light of the above teachings. Therefore, it should be understood at this time that the disclosed interactive, intracardiac signal simulator may be practiced otherwise than as specifically described herein. It is contemplated that various combinations or sub-combinations of the specific features and aspects of the embodiments disclosed above may be made and still fall within the scope of the present disclosure. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with, or substituted for, one another in order to form varying modes of the disclosed interactive, intracardiac signal simulator. Thus, it is intended that the scope of the present interactive, intracardiac signal simulation system, apparatus and methods herein disclosed should not be limited by the particular embodiments described above. Moreover, while the interactive, intracardiac signal simulation system, apparatus and methods are susceptible to various modifications, and alternative forms, specific examples thereof have been shown in the drawings and are herein described in detail. It should be understood, however, that the interactive, intracardiac signal simulation system, apparatus and methods are not to be limited to the particular forms or methods disclosed, but to the contrary, the interactive, intracardiac signal simulation system, apparatus and methods are to cover all modifications, equivalents, and alternatives falling within the spirit and scope of the various embodiments described herein. Any methods disclosed herein need not be performed in the order recited. The methods disclosed herein include certain actions taken by a practitioner; however, they can also include any third-party instruction of those actions, either expressly or by implication. For example, actions such as "discriminating between two populations" include "instructing the discriminating between two populations." The ranges disclosed herein also encompass any and all overlap, sub-ranges, and combinations thereof. Language such as "up to," "at least," "greater than," "less than," "between," and the like include the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. An interactive intracardiac simulation system configured to interface with an electrophysiological (EP) recording system and dynamically simulate an electrical behavior of a patient's heart in response to user inputs, the system comprising:
    a computer comprising a processor, a memory device, a storage device and a network interface device;
    a hardware interface board, in communication with the computer and with the electrophysiological recording system, the hardware interface board configured to detect, convert, and condition simulated cardiac signals transmitted to and received from the electrophysiological recording system;
    a user interface in communication with the processor, the user interface including a display device; and
    a cardiac model, configured to execute on the computer, the cardiac model comprising a plurality of state machines each configured to represent a structural portion of a patient's heart,
    wherein the plurality of state machines are connected via links that simulate conduction pathways between the structural portions of the patient's heart such that the system is configured to simulate cardiac arrhythmias, the structural portions of the patient's heart comprising at least the sinoatrial node, the atrioventricular node, the right ventricle, the left ventricle, the His bundle, and the coronary sinus;
    wherein each of the plurality of state machines is switchable between a resting state and a refractory state,
    wherein each of the plurality of state machines includes a refractory timer having a programmable refractory period, the refractory timer configured to time the expiration of the refractory period in response to a transition of the associated state machine to the refractory state,
    wherein, in response to one or more of the plurality of state machines switching from the resting state to the refractory state, the programmable refractory period is dynamically determined and reset such that the refractory period is based on, at least in part, an exponential decay function having a decay rate that depends, at least in part, on a current cycle time of the associated state machine and/or a current diastolic interval of the associated state machine,
    wherein each of the plurality of state machines includes a cycle length timer having a programmable cycle length period, the cycle length timer configured to time the expiration of the cycle length period in response to a transition of the associated state machine to the resting state,
    wherein, in response to one or more of the plurality of state machines switching to the resting state, the programmable cycle length period is dynamically determined and reset such that the cycle length period is based on, at least in part, an exponential decay function having a decay rate that depends on, at least in part, a current cycle time of the associated state machine and/or a current diastolic interval of the associated state machine, and
    wherein in response to expiration of the dynamically determined and reset programmable refractory period or cycle length period, the refractory timer or cycle length timer causes a state transition signal to be transmitted.

2. The simulation system of claim 1, wherein resetting the refractory period or cycle length period is based on, at least in part, an exponential decay function having a decay rate that depends, at least in part, on a random process.

3. The simulation system of claim 2, wherein the random process is a uniform probability density function, a Gaussian probability density function, or a Poisson distribution function, and a Laplace distribution function.

4. The simulation system of claim 1, wherein the cardiac model is configured to generate a simulated cardiac signal and to transmit the simulated cardiac signal to the user interface and to the hardware interface board.

5. The simulation system of claim 4, further comprising a stimulation module, configured to execute on the computer, the stimulation module configured to compare a signal received from the electrophysiological recording system with the generated simulated cardiac signal, wherein in response to a determination that the compared signals differ beyond a predetermined threshold, a notification that a pacing pulse has been detected is transmitted to the cardiac model.

6. The simulation system of claim 1, further comprising a visualization module, configured to execute on the computer, the visualization module further configured to generate a simulated surface electrocardiogram signal and a simulated intracardiac electrogram signal and to transmit the simulated surface electrocardiogram and intracardiac electrogram signals to the user interface.

7. A method for simulating arrhythmias of a heart using an interactive intracardiac simulation system, the method comprising:
    defining a plurality of structural portions of a cardiac anatomy;
    defining conduction pathways between the structural portions of the cardiac anatomy;
    associating a state machine with each of the defined structural portions of the cardiac anatomy, associating a link with each of the defined conduction pathways between the structural portions of the cardiac anatomy, the structural portions of the cardiac anatomy comprising at least the sinoatrial node, the atrioventricular node, the right ventricle, the left ventricle, the His bundle, and the coronary sinus, the associated state machines configured to execute on a computer, the computer comprising a processor, a memory device, a storage device, an input/output device, and a network interface device, wherein each associated state machine is switchable between a resting state and a refractory state;

associating, with each associated state machine, a refractory timer having a programmable refractory period, the refractory timer configured to time the expiration of the refractory period in response to a transition of the associated state machine to the refractory state; and resetting, in response to the transition of the associated state machine to the refractory state, wherein resetting the refractory period is based on, at least in part, an exponential decay function having a decay rate that depends, at least in part, on a current cycle time of the associated state machine and/or a current diastolic interval of the associated state machine of the associated state machine.

8. The method of claim 7, wherein resetting the refractory period is based on, at least in part, an exponential decay function having a decay rate that depends, at least in part, on a random process.

9. The method of claim 7, further comprising:
associating, with each associated state machine, a cycle length timer having a dynamically programmable cycle length period, the cycle length timer configured to time the expiration of the cycle length period in response to a transition of the associated state machine to the resting state; and
resetting, in response to a transition of the associated state machine to the resting state, the cycle length period, the reset cycle length period based on, at least in part, a current cycle time of the associated state machine, a current diastolic interval of the associated state machine, both the current cycle time and the current diastolic interval of the associated state machine, or a random process.

10. The method of claim 9, wherein resetting the cycle length period is based on, at least in part, an exponential decay function having a decay rate that depends on, at least in part, a current cycle time of the associated state machine, a current diastolic interval of the associated state machine, both the current cycle time and the current diastolic interval of the associated state machine, or a random process.

11. The method of claim 7, further comprising:
detecting the states of the associated state machines;
generating a simulated surface electrocardiogram (ECG) and a simulated intracardiac electrogram (IEGM) based on the detected states of the associated state machines;
transmitting, to an instructor workstation and to a hardware interface board, the simulated surface ECG and IEGM signals;
displaying, on the instructor workstation, the simulated surface ECG and IEGM signals;
processing, on the hardware interface board, the simulated surface ECG and IEGM signals; and
transmitting, from the hardware interface board to an electrophysiological (EP) recording system, the processed simulated surface ECG and IEGM signals.

12. The method of claim 11, further comprising:
receiving, from the electrophysiological recording system, a plurality of EP signals reflective of signals received by the electrophysiological recording system;
comparing the received EP signals with the transmitted processed simulated surface ECG and IEGM signals; and
determining, in response an assessment that the compared signals differ beyond a predetermined threshold, that a pacing stimulus has been detected.

13. The method of claim 11, further comprising:
receiving, from the instructor workstation, an instruction to modify at least one of the plurality of associated state machines; and
modifying, in response to the instruction, the at least one of the plurality of associated state machines.

* * * * *